(12) United States Patent
Baldasarre et al.

(10) Patent No.: US 12,260,050 B2
(45) Date of Patent: Mar. 25, 2025

(54) DIFFERENTIAL RECEIVE AT AN ULTRASONIC TRANSDUCER

(71) Applicant: TDK CORPORATION, Tokyo (JP)

(72) Inventors: Leonardo Baldasarre, Varese (IT); Alessandro Colombo, Milan (IT); Federica Confalonieri, Carimate (IT); Marco Travagliati, Pavia (IT)

(73) Assignee: TDK CORPORATION, Tokyo (JP)

( * ) Notice: Subject to any disclaimer, the term of this patent is extended or adjusted under 35 U.S.C. 154(b) by 33 days.

(21) Appl. No.: 17/822,116

(22) Filed: Aug. 24, 2022

(65) Prior Publication Data

US 2023/0065212 A1 Mar. 2, 2023

Related U.S. Application Data

(60) Provisional application No. 63/260,571, filed on Aug. 25, 2021.

(51) Int. Cl.
  *G06F 3/043* (2006.01)
  *A61B 8/00* (2006.01)
  (Continued)

(52) U.S. Cl.
  CPC .......... *G06F 3/0436* (2013.01); *A61B 8/4483* (2013.01); *B06B 1/0207* (2013.01);
  (Continued)

(58) Field of Classification Search
  CPC ....... A61B 8/4483; A61B 8/00; G06F 3/0436; G06V 40/1306; B06B 1/0207; B06B 1/064
  See application file for complete search history.

(56) References Cited

U.S. PATENT DOCUMENTS

| | | | |
|---|---|---|---|
| 4,880,012 A | 11/1989 | Sato | |
| 5,575,286 A | 11/1996 | Weng et al. | |

(Continued)

FOREIGN PATENT DOCUMENTS

| | | | |
|---|---|---|---|
| CN | 1826631 A | 8/2006 | |
| CN | 101192644 A | 6/2008 | |

(Continued)

OTHER PUBLICATIONS

Tang, et al., "Pulse-Echo Ultrasonic Fingerprint Sensor on a Chip", IEEE Transducers, Anchorage, Alaska, USA, Jun. 21-25, 2015, pp. 674-677.

(Continued)

*Primary Examiner* — Chao Sheng

(57) ABSTRACT

An ultrasonic transducer device including a substrate, an edge support structure connected to the substrate, and a membrane connected to the edge support structure such that a cavity is defined between the membrane and the substrate, the membrane configured to allow movement at ultrasonic frequencies. The membrane includes a structural layer, a piezoelectric layer having a first surface and a second surface, a first electrode placed on the first surface of the piezoelectric layer, wherein the first electrode is located at the center of the membrane, a second electrode placed on the first surface of the piezoelectric layer, wherein the second electrode is a patterned electrode comprising more than one electrode components that are electrically coupled, and a third electrode coupled to the second surface of the piezoelectric layer and electrically coupled to ground.

18 Claims, 6 Drawing Sheets

(51) Int. Cl.
  *B06B 1/02* (2006.01)
  *B06B 1/06* (2006.01)
  *G06V 40/13* (2022.01)
(52) U.S. Cl.
  CPC ............ *G06V 40/1306* (2022.01); *A61B 8/00* (2013.01); *B06B 1/064* (2013.01)

(56) References Cited

U.S. PATENT DOCUMENTS

| | | |
|---|---|---|
| 5,680,863 A | 10/1997 | Hossack et al. |
| 5,684,243 A | 11/1997 | Gururaja et al. |
| 5,808,967 A | 9/1998 | Yu et al. |
| 5,867,302 A | 2/1999 | Fleming |
| 5,911,692 A | 6/1999 | Hussain et al. |
| 6,071,239 A | 6/2000 | Cribbs et al. |
| 6,104,673 A | 8/2000 | Cole et al. |
| 6,289,112 B1 | 9/2001 | Jain et al. |
| 6,292,576 B1 | 9/2001 | Brownlee |
| 6,296,610 B1 | 10/2001 | Schneider et al. |
| 6,350,652 B1 | 2/2002 | Libera et al. |
| 6,428,477 B1 | 8/2002 | Mason |
| 6,483,932 B1 | 11/2002 | Martinez et al. |
| 6,500,120 B1 | 12/2002 | Anthony |
| 6,676,602 B1 | 1/2004 | Barnes et al. |
| 6,679,844 B2 | 1/2004 | Loftman et al. |
| 6,736,779 B1 | 5/2004 | Sano et al. |
| 7,067,962 B2 | 6/2006 | Scott |
| 7,109,642 B2 | 9/2006 | Scott |
| 7,243,547 B2 | 7/2007 | Cobianu et al. |
| 7,257,241 B2 | 8/2007 | Lo |
| 7,400,750 B2 | 7/2008 | Nam |
| 7,433,034 B1 | 10/2008 | Huang |
| 7,459,836 B2 | 12/2008 | Scott |
| 7,471,034 B2 | 12/2008 | Schlote-Holubek et al. |
| 7,489,066 B2 | 2/2009 | Scott et al. |
| 7,634,117 B2 | 12/2009 | Cho |
| 7,665,763 B2 | 2/2010 | Bjoerklund et al. |
| 7,739,912 B2 | 6/2010 | Schneider et al. |
| 7,914,454 B2 | 3/2011 | Weber et al. |
| 8,018,010 B2 | 9/2011 | Tigli et al. |
| 8,139,827 B2 | 3/2012 | Schneider et al. |
| 8,255,698 B2 | 8/2012 | Li et al. |
| 8,311,514 B2 | 11/2012 | Bandyopadhyay et al. |
| 8,335,356 B2 | 12/2012 | Schmitt |
| 8,433,110 B2 | 4/2013 | Kropp et al. |
| 8,508,103 B2 | 8/2013 | Schmitt et al. |
| 8,515,135 B2 | 8/2013 | Clarke et al. |
| 8,666,126 B2 | 3/2014 | Lee et al. |
| 8,703,040 B2 | 4/2014 | Liufu et al. |
| 8,723,399 B2 | 5/2014 | Sammoura et al. |
| 8,805,031 B2 | 8/2014 | Schmitt |
| 9,056,082 B2 | 6/2015 | Liautaud et al. |
| 9,070,861 B2 | 6/2015 | Bibl et al. |
| 9,224,030 B2 | 12/2015 | Du et al. |
| 9,245,165 B2 | 1/2016 | Slaby et al. |
| 9,424,456 B1 | 8/2016 | Kamath Koteshwara et al. |
| 9,572,549 B2 | 2/2017 | Belevich et al. |
| 9,582,102 B2 | 2/2017 | Setlak |
| 9,582,705 B2 | 2/2017 | Du et al. |
| 9,607,203 B1 | 3/2017 | Yazdandoost et al. |
| 9,607,206 B2 | 3/2017 | Schmitt et al. |
| 9,613,246 B1 | 4/2017 | Gozzini et al. |
| 9,618,405 B2 | 4/2017 | Liu et al. |
| 9,665,763 B2 | 5/2017 | Du et al. |
| 9,747,488 B2 | 8/2017 | Yazdandoost et al. |
| 9,785,819 B1 | 10/2017 | Oreifej |
| 9,815,087 B2 | 11/2017 | Ganti et al. |
| 9,817,108 B2 | 11/2017 | Kuo et al. |
| 9,818,020 B2 | 11/2017 | Schuckers et al. |
| 9,881,195 B2 | 1/2018 | Lee et al. |
| 9,881,198 B2 | 1/2018 | Lee et al. |
| 9,898,640 B2 | 2/2018 | Ghavanini |
| 9,904,836 B2 | 2/2018 | Yeke Yazdandoost et al. |
| 9,909,225 B2 | 3/2018 | Lee et al. |
| 9,922,235 B2 | 3/2018 | Cho et al. |
| 9,933,319 B2 | 4/2018 | Li et al. |
| 9,934,371 B2 | 4/2018 | Hong et al. |
| 9,939,972 B2 | 4/2018 | Shepelev et al. |
| 9,953,205 B1 | 4/2018 | Rasmussen et al. |
| 9,959,444 B2 | 5/2018 | Young et al. |
| 9,967,100 B2 | 5/2018 | Hong et al. |
| 9,983,656 B2 | 5/2018 | Merrell et al. |
| 9,984,271 B1 | 5/2018 | King et al. |
| 10,006,824 B2 | 6/2018 | Tsai et al. |
| 10,080,544 B2 | 9/2018 | Chiang et al. |
| 10,275,638 B1 | 4/2019 | Yousefpor et al. |
| 10,315,222 B2 | 6/2019 | Salvia et al. |
| 10,322,929 B2 | 6/2019 | Soundara Pandian et al. |
| 10,325,915 B2 | 6/2019 | Salvia et al. |
| 10,387,704 B2 | 8/2019 | Dagan et al. |
| 10,445,547 B2 | 10/2019 | Tsai |
| 10,461,124 B2 | 10/2019 | Berger et al. |
| 10,478,858 B2 | 11/2019 | Lasiter et al. |
| 10,488,274 B2 | 11/2019 | Li et al. |
| 10,497,747 B2 | 12/2019 | Tsai et al. |
| 10,515,255 B2 | 12/2019 | Strohmann et al. |
| 10,539,539 B2 | 1/2020 | Garlepp et al. |
| 10,562,070 B2 | 2/2020 | Garlepp et al. |
| 10,600,403 B2 | 3/2020 | Garlepp et al. |
| 10,643,052 B2 | 5/2020 | Garlepp et al. |
| 10,656,255 B2 | 5/2020 | Ng et al. |
| 10,670,716 B2 | 6/2020 | Apte et al. |
| 10,706,835 B2 | 7/2020 | Garlepp et al. |
| 10,726,231 B2 | 7/2020 | Tsai et al. |
| 10,755,067 B2 | 8/2020 | De Foras et al. |
| 11,107,858 B2 | 8/2021 | Berger et al. |
| 11,112,388 B2 | 9/2021 | Garlepp et al. |
| 11,301,552 B2 | 4/2022 | Gurin et al. |
| 2001/0016686 A1 | 8/2001 | Okada et al. |
| 2001/0051772 A1 | 12/2001 | Bae |
| 2002/0062086 A1 | 5/2002 | Miele et al. |
| 2002/0135273 A1 | 9/2002 | Mauchamp et al. |
| 2003/0013955 A1 | 1/2003 | Poland |
| 2004/0059220 A1 | 3/2004 | Mourad et al. |
| 2004/0085858 A1 | 5/2004 | Khuri-Yakub et al. |
| 2004/0122316 A1 | 6/2004 | Satoh et al. |
| 2004/0174773 A1 | 9/2004 | Thomenius et al. |
| 2005/0023937 A1 | 2/2005 | Sashida et al. |
| 2005/0057284 A1 | 3/2005 | Wodnicki |
| 2005/0094490 A1 | 5/2005 | Thomenius et al. |
| 2005/0100200 A1 | 5/2005 | Abiko et al. |
| 2005/0110071 A1 | 5/2005 | Ema et al. |
| 2005/0146240 A1 | 7/2005 | Smith et al. |
| 2005/0148132 A1 | 7/2005 | Wodnicki et al. |
| 2005/0162040 A1 | 7/2005 | Robert |
| 2005/0228277 A1 | 10/2005 | Barnes et al. |
| 2006/0052697 A1 | 3/2006 | Hossack et al. |
| 2006/0079773 A1 | 4/2006 | Mourad et al. |
| 2006/0079777 A1 | 4/2006 | Karasawa |
| 2006/0210130 A1 | 9/2006 | Germond-Rouet et al. |
| 2006/0230605 A1 | 10/2006 | Schlote-Holubek et al. |
| 2006/0280346 A1 | 12/2006 | Machida |
| 2007/0016026 A1 | 1/2007 | Thomenius et al. |
| 2007/0046396 A1 | 3/2007 | Huang |
| 2007/0047785 A1 | 3/2007 | Jang et al. |
| 2007/0073135 A1 | 3/2007 | Lee et al. |
| 2007/0164632 A1 | 7/2007 | Adachi et al. |
| 2007/0202252 A1 | 8/2007 | Sasaki |
| 2007/0215964 A1 | 9/2007 | Khuri-Yakub et al. |
| 2007/0223791 A1 | 9/2007 | Shinzaki |
| 2007/0230754 A1 | 10/2007 | Jain et al. |
| 2008/0125660 A1 | 5/2008 | Yao et al. |
| 2008/0146938 A1 | 6/2008 | Hazard et al. |
| 2008/0150032 A1 | 6/2008 | Tanaka |
| 2008/0194053 A1 | 8/2008 | Huang |
| 2008/0240523 A1 | 10/2008 | Benkley et al. |
| 2009/0005684 A1 | 1/2009 | Kristoffersen et al. |
| 2009/0163805 A1 | 6/2009 | Sunagawa et al. |
| 2009/0171213 A1 | 7/2009 | Savord |
| 2009/0182237 A1 | 7/2009 | Angelsen et al. |
| 2009/0232367 A1 | 9/2009 | Shinzaki |
| 2009/0274343 A1 | 11/2009 | Clarke |
| 2009/0303838 A1 | 12/2009 | Svet |
| 2010/0030076 A1 | 2/2010 | Vortman et al. |

(56) References Cited

U.S. PATENT DOCUMENTS

| | | |
|---|---|---|
| 2010/0046810 A1 | 2/2010 | Yamada |
| 2010/0063391 A1 | 3/2010 | Kanai et al. |
| 2010/0113952 A1 | 5/2010 | Raguin et al. |
| 2010/0168583 A1 | 7/2010 | Dausch et al. |
| 2010/0195851 A1 | 8/2010 | Buccafusca |
| 2010/0201222 A1 | 8/2010 | Adachi et al. |
| 2010/0202254 A1 | 8/2010 | Roest et al. |
| 2010/0208004 A1 | 8/2010 | Ottosson et al. |
| 2010/0239751 A1 | 9/2010 | Regniere |
| 2010/0251824 A1 | 10/2010 | Schneider et al. |
| 2010/0256498 A1 | 10/2010 | Tanaka |
| 2010/0278008 A1 | 11/2010 | Ammar |
| 2011/0285244 A1 | 11/2011 | Lewis et al. |
| 2011/0291207 A1 | 12/2011 | Martin et al. |
| 2011/0319767 A1 | 12/2011 | Tsuruno |
| 2012/0016604 A1 | 1/2012 | Irving et al. |
| 2012/0092026 A1 | 4/2012 | Liautaud et al. |
| 2012/0095335 A1 | 4/2012 | Sverdlik et al. |
| 2012/0095344 A1 | 4/2012 | Kristoffersen et al. |
| 2012/0095347 A1 | 4/2012 | Adam et al. |
| 2012/0147698 A1 | 6/2012 | Wong et al. |
| 2012/0179044 A1 | 7/2012 | Chiang et al. |
| 2012/0224041 A1 | 9/2012 | Monden |
| 2012/0232396 A1 | 9/2012 | Tanabe |
| 2012/0238876 A1 | 9/2012 | Tanabe et al. |
| 2012/0263355 A1 | 10/2012 | Monden |
| 2012/0279865 A1 | 11/2012 | Regniere et al. |
| 2012/0288641 A1 | 11/2012 | Diatezua et al. |
| 2012/0300988 A1 | 11/2012 | Ivanov et al. |
| 2013/0051179 A1 | 2/2013 | Hong |
| 2013/0064043 A1 | 3/2013 | Degertekin et al. |
| 2013/0127297 A1 | 5/2013 | Bautista et al. |
| 2013/0127592 A1 | 5/2013 | Fyke et al. |
| 2013/0133428 A1 | 5/2013 | Lee et al. |
| 2013/0201134 A1 | 8/2013 | Schneider et al. |
| 2013/0271628 A1 | 10/2013 | Ku et al. |
| 2013/0294201 A1 | 11/2013 | Hajati |
| 2013/0294202 A1 | 11/2013 | Hajati |
| 2014/0003679 A1 | 1/2014 | Han et al. |
| 2014/0060196 A1 | 3/2014 | Falter et al. |
| 2014/0117812 A1 | 5/2014 | Hajati |
| 2014/0176332 A1 | 6/2014 | Alameh et al. |
| 2014/0208853 A1 | 7/2014 | Onishi et al. |
| 2014/0219521 A1 | 8/2014 | Schmitt et al. |
| 2014/0232241 A1 | 8/2014 | Hajati |
| 2014/0265721 A1 | 9/2014 | Robinson et al. |
| 2014/0294262 A1 | 10/2014 | Schuckers et al. |
| 2014/0313007 A1 | 10/2014 | Harding |
| 2014/0355387 A1 | 12/2014 | Kitchens et al. |
| 2015/0036065 A1 | 2/2015 | Yousefpor et al. |
| 2015/0049590 A1 | 2/2015 | Rowe et al. |
| 2015/0087991 A1 | 3/2015 | Chen et al. |
| 2015/0097468 A1 | 4/2015 | Hajati et al. |
| 2015/0105663 A1 | 4/2015 | Kiyose et al. |
| 2015/0127965 A1 | 5/2015 | Hong et al. |
| 2015/0145374 A1 | 5/2015 | Xu et al. |
| 2015/0164473 A1 | 6/2015 | Kim et al. |
| 2015/0165479 A1 | 6/2015 | Lasiter et al. |
| 2015/0169136 A1 | 6/2015 | Ganti et al. |
| 2015/0189136 A1 | 7/2015 | Chung et al. |
| 2015/0198699 A1 | 7/2015 | Kuo et al. |
| 2015/0206738 A1 | 7/2015 | Rastegar |
| 2015/0213180 A1 | 7/2015 | Herberholz |
| 2015/0220767 A1 | 8/2015 | Yoon et al. |
| 2015/0241393 A1 | 8/2015 | Ganti et al. |
| 2015/0261261 A1 | 9/2015 | Bhagavatula et al. |
| 2015/0286312 A1 | 10/2015 | Kang et al. |
| 2015/0301653 A1 | 10/2015 | Urushi |
| 2015/0324569 A1 | 11/2015 | Hong et al. |
| 2015/0345987 A1 | 12/2015 | Hajati |
| 2015/0357375 A1 | 12/2015 | Tsai et al. |
| 2015/0358740 A1 | 12/2015 | Tsai et al. |
| 2015/0362589 A1 | 12/2015 | Tsai |
| 2015/0371398 A1 | 12/2015 | Qiao et al. |
| 2016/0026840 A1 | 1/2016 | Li et al. |
| 2016/0041047 A1 | 2/2016 | Liu et al. |
| 2016/0051225 A1 | 2/2016 | Kim et al. |
| 2016/0063294 A1 | 3/2016 | Du et al. |
| 2016/0063300 A1 | 3/2016 | Du et al. |
| 2016/0070967 A1 | 3/2016 | Du et al. |
| 2016/0070968 A1 | 3/2016 | Gu et al. |
| 2016/0086010 A1 | 3/2016 | Merrell et al. |
| 2016/0091378 A1 | 3/2016 | Tsai et al. |
| 2016/0092715 A1 | 3/2016 | Yazdandoost et al. |
| 2016/0092716 A1 | 3/2016 | Yazdandoost et al. |
| 2016/0100822 A1 | 4/2016 | Kim et al. |
| 2016/0107194 A1* | 4/2016 | Panchawagh ......... B06B 1/0666 310/317 |
| 2016/0117541 A1 | 4/2016 | Lu et al. |
| 2016/0180142 A1 | 6/2016 | Riddle et al. |
| 2016/0240768 A1 | 8/2016 | Fujii et al. |
| 2016/0296975 A1 | 10/2016 | Lukacs et al. |
| 2016/0299014 A1 | 10/2016 | Li et al. |
| 2016/0326477 A1 | 11/2016 | Fernandez-Alcon et al. |
| 2016/0345930 A1 | 12/2016 | Mizukami et al. |
| 2016/0350573 A1 | 12/2016 | Kitchens et al. |
| 2016/0358003 A1 | 12/2016 | Shen et al. |
| 2017/0004346 A1 | 1/2017 | Kim et al. |
| 2017/0004352 A1 | 1/2017 | Jonsson et al. |
| 2017/0330552 A1 | 1/2017 | Garlepp et al. |
| 2017/0032485 A1 | 2/2017 | Vemury |
| 2017/0059380 A1 | 3/2017 | Li et al. |
| 2017/0075700 A1 | 3/2017 | Abudi et al. |
| 2017/0076132 A1 | 3/2017 | Sezan et al. |
| 2017/0090024 A1 | 3/2017 | Kitchens et al. |
| 2017/0100091 A1 | 4/2017 | Eigil et al. |
| 2017/0110504 A1 | 4/2017 | Panchawagh et al. |
| 2017/0119343 A1 | 5/2017 | Pintoffl |
| 2017/0124374 A1 | 5/2017 | Rowe et al. |
| 2017/0168543 A1 | 6/2017 | Dai et al. |
| 2017/0185821 A1 | 6/2017 | Chen et al. |
| 2017/0194934 A1 | 7/2017 | Shelton et al. |
| 2017/0200054 A1 | 7/2017 | Du et al. |
| 2017/0219536 A1 | 8/2017 | Koch et al. |
| 2017/0231534 A1 | 8/2017 | Agassy et al. |
| 2017/0243049 A1 | 8/2017 | Dong |
| 2017/0255338 A1 | 9/2017 | Medina et al. |
| 2017/0293791 A1 | 10/2017 | Mainguet et al. |
| 2017/0316243 A1 | 11/2017 | Ghavanini |
| 2017/0316248 A1 | 11/2017 | He et al. |
| 2017/0322290 A1 | 11/2017 | Ng |
| 2017/0322291 A1 | 11/2017 | Salvia et al. |
| 2017/0322292 A1 | 11/2017 | Salvia et al. |
| 2017/0322305 A1 | 11/2017 | Apte et al. |
| 2017/0323133 A1 | 11/2017 | Tsai |
| 2017/0325081 A1 | 11/2017 | Chrisikos et al. |
| 2017/0326590 A1 | 11/2017 | Daneman |
| 2017/0326591 A1 | 11/2017 | Apte et al. |
| 2017/0326593 A1 | 11/2017 | Garlepp et al. |
| 2017/0326594 A1 | 11/2017 | Berger et al. |
| 2017/0328866 A1 | 11/2017 | Apte et al. |
| 2017/0328870 A1 | 11/2017 | Garlepp et al. |
| 2017/0330012 A1 | 11/2017 | Salvia et al. |
| 2017/0330553 A1 | 11/2017 | Garlepp et al. |
| 2017/0344782 A1 | 11/2017 | Andersson |
| 2017/0357839 A1 | 12/2017 | Yazdandoost et al. |
| 2017/0368574 A1 | 12/2017 | Sammoura et al. |
| 2018/0025202 A1 | 1/2018 | Ryshtun et al. |
| 2018/0032788 A1 | 2/2018 | Krenzer et al. |
| 2018/0069168 A1* | 3/2018 | Ikeuchi ................. H10N 30/40 |
| 2018/0101711 A1 | 4/2018 | D'Souza et al. |
| 2018/0107852 A1 | 4/2018 | Fenrich et al. |
| 2018/0107854 A1 | 4/2018 | Tsai et al. |
| 2018/0129849 A1 | 5/2018 | Strohmann et al. |
| 2018/0129857 A1 | 5/2018 | Bonev |
| 2018/0150679 A1 | 5/2018 | Kim et al. |
| 2018/0178251 A1 | 6/2018 | Foncellino et al. |
| 2018/0206820 A1 | 7/2018 | Anand et al. |
| 2018/0217008 A1 | 8/2018 | Li et al. |
| 2018/0225495 A1 | 8/2018 | Jonsson et al. |
| 2018/0229267 A1 | 8/2018 | Ono et al. |
| 2018/0268232 A1 | 9/2018 | Kim et al. |
| 2018/0276443 A1 | 9/2018 | Strohmann et al. |
| 2018/0276672 A1 | 9/2018 | Breed et al. |

(56) References Cited

U.S. PATENT DOCUMENTS

| | | | |
|---|---|---|---|
| 2018/0329560 A1 | 11/2018 | Kim et al. | |
| 2018/0341799 A1 | 11/2018 | Schwartz et al. | |
| 2018/0349663 A1 | 12/2018 | Garlepp et al. | |
| 2018/0357457 A1 | 12/2018 | Rasmussen et al. | |
| 2018/0369866 A1 | 12/2018 | Sammoura et al. | |
| 2018/0373913 A1 | 12/2018 | Panchawagh et al. | |
| 2018/0376253 A1 | 12/2018 | Lutsky et al. | |
| 2019/0005300 A1 | 1/2019 | Garlepp et al. | |
| 2019/0012673 A1 | 1/2019 | Chakraborty et al. | |
| 2019/0018123 A1 | 1/2019 | Narasimha-Iyer et al. | |
| 2019/0043920 A1 | 2/2019 | Berger et al. | |
| 2019/0046263 A1 | 2/2019 | Hayashida et al. | |
| 2019/0057267 A1 | 2/2019 | Kitchens et al. | |
| 2019/0073507 A1 | 3/2019 | D'Souza et al. | |
| 2019/0087632 A1 | 3/2019 | Raguin et al. | |
| 2019/0095015 A1 | 3/2019 | Han et al. | |
| 2019/0102046 A1 | 4/2019 | Miranto et al. | |
| 2019/0130083 A1 | 5/2019 | Agassy et al. | |
| 2019/0148619 A1* | 5/2019 | Ikeuchi | H10N 30/853 310/357 |
| 2019/0171858 A1 | 6/2019 | Ataya et al. | |
| 2019/0175035 A1 | 6/2019 | Van Der Horst et al. | |
| 2019/0180069 A1 | 6/2019 | Akhbari et al. | |
| 2019/0188441 A1 | 6/2019 | Hall et al. | |
| 2019/0188442 A1 | 6/2019 | Flament et al. | |
| 2019/0247887 A1 | 8/2019 | Salvia et al. | |
| 2019/0262865 A1 | 8/2019 | Mehdizadeh et al. | |
| 2019/0311177 A1 | 10/2019 | Joo et al. | |
| 2019/0325185 A1 | 10/2019 | Tang | |
| 2019/0340455 A1 | 11/2019 | Jung et al. | |
| 2019/0354238 A1 | 11/2019 | Akhbari et al. | |
| 2019/0370518 A1 | 12/2019 | Maor et al. | |
| 2020/0030850 A1 | 1/2020 | Apte et al. | |
| 2020/0050816 A1 | 2/2020 | Tsai | |
| 2020/0050817 A1 | 2/2020 | Salvia et al. | |
| 2020/0050820 A1 | 2/2020 | Iatsun et al. | |
| 2020/0050828 A1 | 2/2020 | Li et al. | |
| 2020/0074135 A1 | 3/2020 | Garlepp et al. | |
| 2020/0111834 A1 | 4/2020 | Tsai et al. | |
| 2020/0125710 A1 | 4/2020 | Andersson et al. | |
| 2020/0147644 A1* | 5/2020 | Chang | B06B 1/0666 |
| 2020/0158694 A1 | 5/2020 | Garlepp et al. | |
| 2020/0175143 A1 | 6/2020 | Lee et al. | |
| 2020/0194495 A1 | 6/2020 | Berger et al. | |
| 2020/0210666 A1 | 7/2020 | Flament | |
| 2020/0250393 A1 | 8/2020 | Tsai et al. | |
| 2020/0257875 A1 | 8/2020 | Hall et al. | |
| 2020/0285882 A1 | 9/2020 | Skovgaard Christensen et al. | |
| 2020/0302140 A1 | 9/2020 | Lu et al. | |
| 2020/0342203 A1 | 10/2020 | Lin et al. | |
| 2020/0355824 A1 | 11/2020 | Apte et al. | |
| 2020/0400800 A1 | 12/2020 | Ng et al. | |
| 2020/0410070 A1 | 12/2020 | Strohmann | |
| 2020/0410193 A1 | 12/2020 | Wu | |
| 2021/0015456 A1 | 1/2021 | Chiang et al. | |
| 2021/0069748 A1 | 3/2021 | Bircumshaw et al. | |
| 2021/0161503 A1 | 6/2021 | Mashood et al. | |
| 2021/0177378 A1 | 6/2021 | Goericke et al. | |
| 2022/0043144 A1 | 2/2022 | Yanni et al. | |
| 2022/0262161 A1 | 8/2022 | Zhao et al. | |

FOREIGN PATENT DOCUMENTS

| | | |
|---|---|---|
| CN | 102159334 A | 8/2011 |
| CN | 104415902 A | 3/2015 |
| CN | 105264542 A | 1/2016 |
| CN | 105378756 A | 3/2016 |
| CN | 106458575 B | 7/2018 |
| CN | 109196671 A | 1/2019 |
| CN | 109255323 A | 1/2019 |
| CN | 112241657 A | 1/2021 |
| EP | 1214909 A1 | 6/2002 |
| EP | 1768101 A1 | 3/2007 |
| EP | 2884301 A1 | 6/2015 |
| EP | 3086261 A2 | 10/2016 |
| EP | 1534140 B1 | 1/2019 |
| EP | 3292508 B1 | 12/2020 |
| EP | 3757884 A1 | 12/2020 |
| JP | 2011040467 A | 2/2011 |
| JP | 2014183229 A | 9/2014 |
| KR | 20200090355 A | 7/2020 |
| TW | 201531701 A | 8/2015 |
| WO | 2007018635 A1 | 2/2007 |
| WO | 2009096576 A2 | 8/2009 |
| WO | 2009137106 A2 | 11/2009 |
| WO | 2014035564 A1 | 3/2014 |
| WO | 2015009635 A1 | 1/2015 |
| WO | 2015112453 A1 | 7/2015 |
| WO | 2015120132 A1 | 8/2015 |
| WO | 2015131083 A1 | 9/2015 |
| WO | 2015134816 A1 | 9/2015 |
| WO | 2015183945 A1 | 12/2015 |
| WO | 2015193917 A2 | 12/2015 |
| WO | 2016007250 A1 | 1/2016 |
| WO | 2016011172 A1 | 1/2016 |
| WO | 2016022439 A1 | 2/2016 |
| WO | 2016040333 A2 | 3/2016 |
| WO | 2016053587 A1 | 4/2016 |
| WO | 2016061406 A1 | 4/2016 |
| WO | 2016061410 A1 | 4/2016 |
| WO | 2017003848 A1 | 1/2017 |
| WO | 2017053877 A2 | 3/2017 |
| WO | 2017192890 A1 | 11/2017 |
| WO | 2017192895 A1 | 11/2017 |
| WO | 2017192899 A1 | 11/2017 |
| WO | 2017196678 A1 | 11/2017 |
| WO | 2017196681 A1 | 11/2017 |
| WO | 2017196682 A1 | 11/2017 |
| WO | 2017192903 A3 | 12/2017 |
| WO | 2018148332 A1 | 8/2018 |
| WO | 2019005487 A1 | 1/2019 |
| WO | 2019164721 A1 | 8/2019 |
| WO | 2020081182 A1 | 4/2020 |

OTHER PUBLICATIONS

ISA/EP, International Search Report and Written Opinion for International Application # PCT/US2018/063431, pp. 1-15, mailed Feb. 5, 2019.

ISA/EP, International Search Report and Written Opinion for International Application No. PCT/US2017/031120, 12 pages, Aug. 29, 2017.

ISA/EP, International Search Report and Written Opinion for International Application No. PCT/US2017/031127, 13 pages, Sep. 1, 2017.

ISA/EP, International Search Report and Written Opinion for International Application No. PCT/US2017/031134, 12 pages, Aug. 30, 2017.

ISA/EP, International Search Report and Written Opinion for International Application No. PCT/US2017/031140, 18 pages, Nov. 2, 2017.

ISA/EP, International Search Report and Written Opinion for International Application No. PCT/US2017/031421 13 pages, Jun. 21, 2017.

ISA/EP, International Search Report and Written Opinion for International Application No. PCT/US2017/031426 13 pages, Jun. 22, 2017.

ISA/EP, International Search Report and Written Opinion for International Application No. PCT/US2017/031431, 14 pages, Aug. 1, 2017.

ISA/EP, International Search Report and Written Opinion for International Application No. PCT/US2017/031434, 13 pages, Jun. 26, 2017.

ISA/EP, International Search Report and Written Opinion for International Application No. PCT/US2017/031439, 10 pages, Jun. 20, 2017.

ISA/EP, International Search Report and Written Opinion for International Application No. PCT/US2017/031824, 18 pages, Sep. 22, 2017.

(56) References Cited

OTHER PUBLICATIONS

ISA/EP, International Search Report and Written Opinion for International Application No. PCT/US2017/031827, 16 pages, Aug. 1, 2017.
ISA/EP, International Search Report and Written Opinion for International Application No. PCT/US2017/031831, 12 pages, Jul. 21, 2017.
ISA/EP, International Search Report for International Application No. PCT/US2017/031826, 16 pages, Feb. 27, 2018.
ISA/EP, Partial International Search Report for International Application No. PCT/US2017/031140, 13 pages, Aug. 29, 2017.
ISA/EP, Partial International Search Report for International Application No. PCT/US2017/031823, 12 pages, Nov. 30, 2017.
"Receiver Thermal Noise Threshold", Fisher Telecommunication Services, Satellite Communications. Retrieved from the Internet: URL:https://web.archive.org/web/20171027075705/http//www.fishercom.xyz:80/satellite-communications/receiver-thermal-noise-threshold.html, Oct. 27, 2017, 3.
"ZTE V7 Max. 5,5" smartphone on MediaTeck Helio P10 cpu; Published on Apr. 20, 2016; https://www.youtube.com/watch?v=ncNCbpkGQZU (Year: 2016).
Dausch, et al., "Theory and Operation of 2-D Array Piezoelectric Micromachined Ultrasound Transducers", IEEE Transactions on Ultrasonics, and Frequency Control, vol. 55, No. 11;, Nov. 2008, 2484-2492.
Hopcroft, et al., "Temperature Compensation of a MEMS Resonator Using Quality Factor as a Thermometer", Retrieved from Internet: http://micromachine.stanford.edu/~amanu/linked/MAH_MEMS2006.pdf, 2006, 222-225.
Hopcroft, et al., "Using the temperature dependence of resonator quality factor as a thermometer", Applied Physics Letters 91. Retrieved from Internet: http://micromachine.stanford.edu/~hopcroft/Publications/Hopcroft_QT_ApplPhysLett_91_013505.pdf, 2007, 013505-1-031505-3.
Lee, et al., "Low jitter and temperature stable MEMS oscillators", Frequency Control Symposium (FCS), 2012 IEEE International, May 1-5, 2012.
Li, et al., "Capacitive micromachined ultrasonic transducer for ultra-low pressure measurement: Theoretical study", AIP Advances May 2012. Retrieved from Internet: http://scitation.aip.org/content/aip/journal/adva/5/12/10.1063/1.4939217, 2015, 127231.
Qiu, et al., "Piezoelectric Micromachined Ultrasound Transducer (PMUT) Arrays for Integrated Sensing, Actuation and Imaging", Sensors 15, doi:10.3390/s150408020, Apr. 3, 2015, 8020-8041.
Rozen, et al., "Air-Coupled Aluminum Nitride Piezoelectric Micromachined Ultrasonic Transducers at 0.3 MHZ to 0.9 MHZ", 2015 28th IEEE International Conference on Micro Electro Mechanical Systems (MEMS), IEEE, Jan. 18, 2015, 921-924.
Savoia, et al., "Design and Fabrication of a cMUT Probe for Ultrasound Imaging of Fingerprints", 2010 IEEE International Ultrasonics Symposium Proceedings, Oct. 2010, 1877-1880.
Shen, et al., "Anisotropic Complementary Acoustic Metamaterial for Canceling out Aberrating Layers", American Physical Society, Physical Review X 4.4: 041033., Nov. 19, 2014, 041033-1--041033-7.
Tang, et al., "11.2 3D Ultrasonic Fingerprint Sensor-on-a-Chip", 2016 IEEE International Solid-State Circuits Conference, IEEE, Jan. 31, 2016, 202-203.
Thakar, et al., "Multi-resonator approach to eliminating the temperature dependence of silicon-based timing references", Hilton Head'14. Retrieved from the Internet: http://blog.narotama.ac.id/wp-content/uploads/2014/12/Multi-resonator-approach-to-eliminating-the-temperature-dependance-of-silicon-based-timing-references.pdf, 2014, 415-418.
ISA/EP, Partial International Search Report for International Application No. PCT/US2019/034032, 8 pages, Sep. 12, 2019, 8.
EP Office Action, for Application 17724184.1, mailed Oct. 12, 2021, 6 pages.
EP Office Action, for Application 17725017.2 mailed Feb. 25, 2022, 7 pages.
EP Office Action, mailed Oct. 9, 2021, 6 pages.
European Patent Office, Office Action, App 17725018, pp. 5, Oct. 25, 2021.
European Patent Office, Office Action, App 17725020.6, pp. 4, Oct. 25, 2021.
ISA/EP, International Search Report and Written Opinion for International Application # PCT/US2019/015020, pp. 1-23, mailed Jul. 1, 2019.
ISA/EP, International Search Report and Written Opinion for International Application # PCT/US2019/023440, pp. 1-10, mailed Jun. 4, 2019.
ISA/EP, International Search Report and Written Opinion for International Application No. PCT/US2018/037364, 10 pages, Sep. 3, 2018.
ISA/EP, International Search Report and Written Opinion for International Application No. PCT/US2019061516, 14 pages, Mar. 12, 2020.
ISA/EP, International Search Report and Written Opinion for International Application No. PCT/US2020/033854, 16 pages, Nov. 3, 2020.
ISA/EP, International Search Report and Written Opinion for International Application No. PCT/US2020/039208, 10 pages, Oct. 9, 2020.
ISA/EP, International Search Report and Written Opinion for International Application No. PCT/US2020/039452, 11 pages, Sep. 9, 2020.
ISA/EP, International Search Report and Written Opinion for International Application No. PCT/US2020/042427, 18 pages, Dec. 14, 2020.
ISA/EP, International Search Report and Written Opinion for International Application No. PCT/US2020/042428, 9 pages, Oct. 26, 2020.
ISA/EP, International Search Report and Written Opinion for International Application No. PCT/US2021/021412, 12 pages, Jun. 9, 2021.
ISA/EP, International Search Report and Written Opinion for International Application No. PCT/US2021/021561, 9 pages, Jun. 28, 2021.
ISA/EP, Partial Search Report and Provisional Opinion for International Application No. PCT/US2020/042427, 13 pages, Oct. 26, 2020.
ISA/EP, Partial Search Report for International Application No. PCT/US2020/033854, 10 pages, Sep. 8, 2020.
"Moving Average Filters", Waybackmachine XP05547422, Retrieved from the Internet: URL:https://web.archive.org/web/20170809081353/https//www.analog.com/media/en/technical-documentation/dsp-book/dsp_book_Ch15.pdf—[retrieved on Jan. 24, 2019], Aug. 9, 2017, 1-8.
Office Action for CN App No. 201780029016.7 mailed Mar. 24, 2020, 7 pages.
Office Action for CN App No. 201780029016.7 mailed Sep. 25, 2020, 7 pages.
Office Action for TW App No. 106113266 mailed Jun. 22, 2020, 23 pages.
"Sleep Mode", Wikipedia, Retrieved from the Internet: URL:https://web.archive.org/web/20170908153323/https://en.wikipedia.org/wiki/Sleep_mode [retrieved on Jan. 25, 2019], Sep. 8, 2017, 1-3.
Taiwan Application No. 106114623, 1st Office Action, Dated Aug. 5, 2021, pp. 1-8.
"TMS320C5515 Fingerprint Development Kit (FDK) Hardware Guide", Texas Instruments, Literature No. SPRUFX3, XP055547651, Apr. 1-26, 2010.
Cappelli, et al., "Fingerprint Image Reconstruction from Standard Templates", IEEE Transactions on Pattern Analysis and Machine Intelligence, IEEE Computer Society, vol. 29, No. 9, Sep. 2007, 1489-1503.
Feng, et al., "Fingerprint Reconstruction: From Minutiae to Phase", IEEE Transactions on Pattern Analysis and Machine Intelligence, IEEE Computer Society, vol. 33, No. 2, Feb. 2011, 209-223.
Jiang, et al., "Ultrasonic Fingerprint Sensor with Transmit Beamforming Based on a PMUT Array Bonded to CMOS Circuitry", IEEE Transactions on Ultrasonics Ferroelectrics and Frequency Control, Jan. 1, 2017, 1-9.

(56) References Cited

OTHER PUBLICATIONS

Kumar, et al., "Towards Contactless, Low-Cost and Accurate 3D Fingerprint Identification", IEEE Transactions on Pattern Analysis and Machine Intelligence, IEEE Computer Society, vol. 37, No. 3, Mar. 2015, 681-696.

Pang, et al., "Extracting Valley-Ridge Lines from Point-Cloud-Based 3D Fingerprint Models", IEEE Computer Graphics and Applications, IEEE Service Center, New York, vol. 33, No. 4, Jul./Aug. 2013, 73-81.

Papageorgiou, et al., "Self-Calibration of Ultrasonic Transducers in an Intelligent Data Acquisition System", International Scientific Journal of Computing, 2003, vol. 2, Issue 2 Retrieved Online: URL: https://scholar.google.com/scholar?q=self-calibration+of+ultrasonic+transducers+in+an+intelligent+data+acquisition+system&hl=en&as_sdt=0&as_vis=1&oi=scholart, 2003, 9-15.

Ross, et al., "From Template to Image: Reconstructing Fingerprints from Minutiae Points", IEEE Transactions on Pattern Analysis and Machine Intelligence, IEEE Computer Society, vol. 29, No. 4, Apr. 2007, 644-560.

Tang, et al., "Pulse-echo ultrasonic fingerprint sensor on a chip", 2015 Transducers, 2015 18th International Conference on Solid-State Sensors, Actuators and Microsystems, Apr. 1, 2015, 674-677.

Zhou, et al., "Partial Fingerprint Reconstruction with Improved Smooth Extension", Network and System Security, Springer Berlin Heidelberg, Jun. 3, 2013, 756-762.

ISA/EP, International Search Report and Written Opinion for International Application No. PCT/US2022/075468, 28 pages, Jan. 16, 2023.

Office Action for CN App No. 201780028685.2 mailed Dec. 5, 2022, 11 pages.

Office Action for CN App No. 201780027434.2 mailed Oct. 21, 2022, 10 pages.

Office Action for CN App No. 201780027435.7 mailed Sep. 9, 2022, 9 pages.

Office Action for CN App No. 201780027444.6 mailed Dec. 2, 2022, 17 pages.

Office Action for CN App No. 201780029058.0 mailed Dec. 2, 2022, 9 pages.

Office Action for CN App No. 201780029059.5 mailed Nov. 11, 2022, 11 pages.

Office Action for CN App No. 2020800377355 mailed Aug. 3, 2022, 8 pages.

* cited by examiner

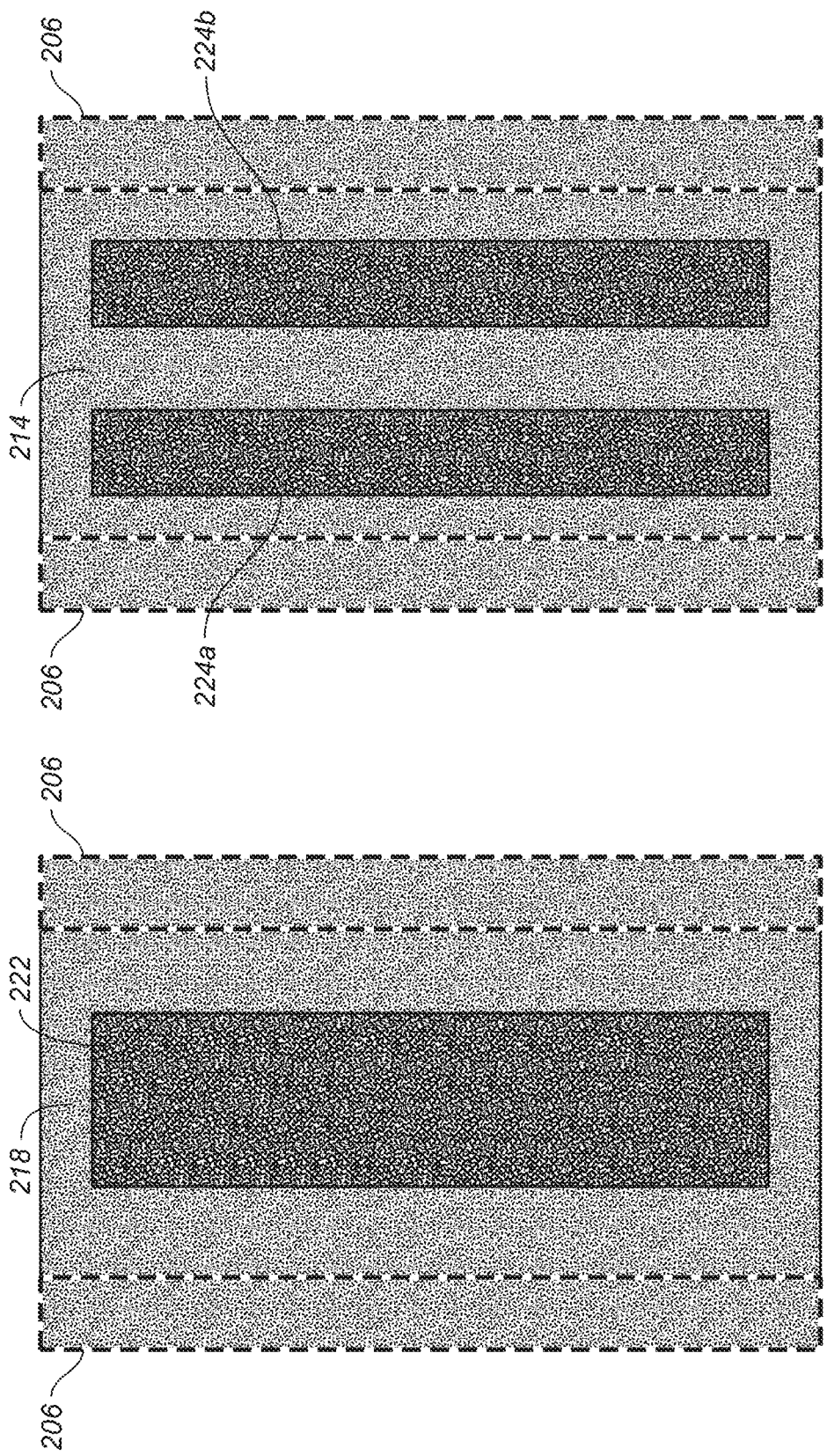

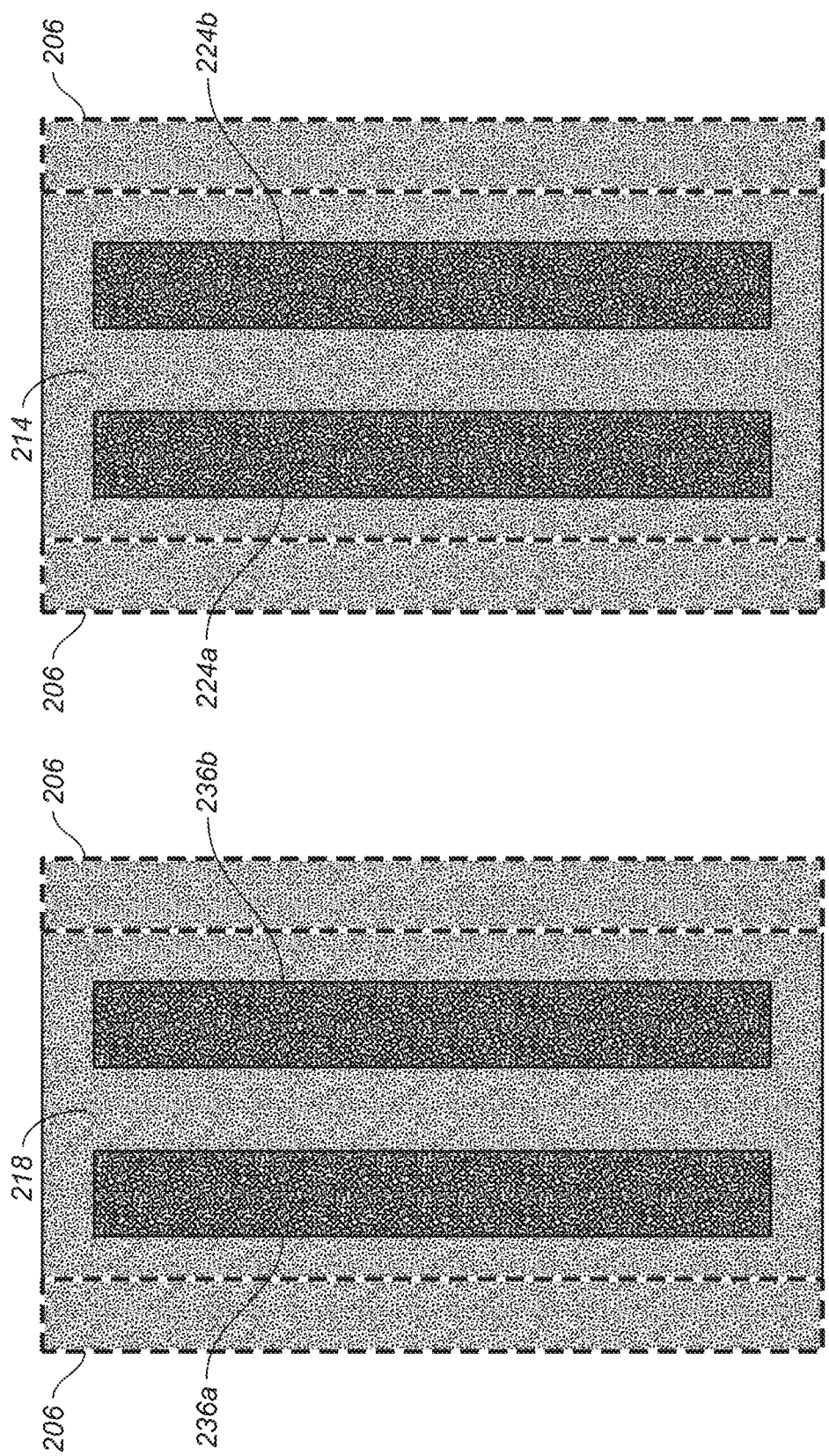

DIFFERENTIAL RECEIVE AT AN ULTRASONIC TRANSDUCER

RELATED APPLICATIONS

This application claims priority to and the benefit of U.S. Patent Provisional Patent Application 63/260,571, filed on Aug. 25, 2021, entitled "SINGLE AND DUAL LAYER PIEZOELECTRIC ULTRASONIC SENSOR," by Baldasarre et al., and assigned to the assignee of the present application, which is incorporated herein by reference in its entirety.

BACKGROUND

Piezoelectric materials facilitate conversion between mechanical energy and electrical energy. Moreover, a piezoelectric material can generate an electrical signal when subjected to mechanical stress, and can vibrate when subjected to an electrical voltage. Piezoelectric materials are widely utilized in piezoelectric ultrasonic transducers to generate acoustic waves based on an actuation voltage applied to electrodes of the piezoelectric ultrasonic transducer.

BRIEF DESCRIPTION OF THE DRAWINGS

The accompanying drawings, which are incorporated in and form a part of the Description of Embodiments, illustrate various embodiments of the subject matter and, together with the Description of Embodiments, serve to explain principles of the subject matter discussed below. Unless specifically noted, the drawings referred to in this Brief Description of Drawings should be understood as not being drawn to scale. Herein, like items are labeled with like item numbers.

FIGS. 3B and 3C are diagrams illustrating views of bottom surfaces of the two piezoelectric layers of an ultrasonic transducer device showing the patterned receive (RX) electrodes, according to some embodiments.

FIGS. 5B and 5C are diagrams illustrating views of bottom surfaces of two piezoelectric layers of an ultrasonic transducer device showing the patterned receive (RX) electrodes, according to other embodiments.

DESCRIPTION OF EMBODIMENTS

Figure 1A:
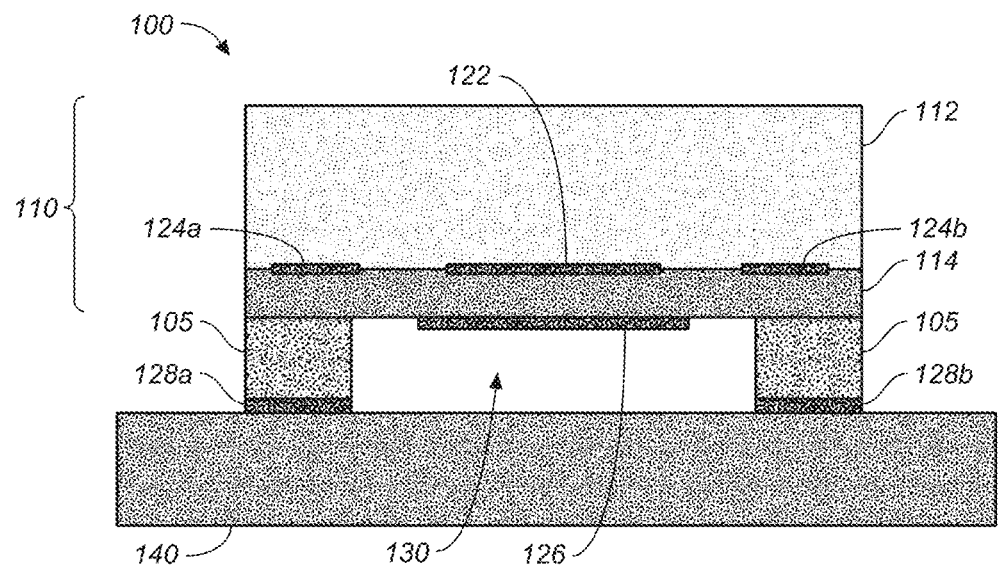
FIG. 1A is a diagram illustrating a side view of an ultrasonic transducer device with a single piezoelectric layer and receive (RX) electrodes on the same plane, according to some embodiments.

The following Description of Embodiments is merely provided by way of example and not of limitation. Furthermore, there is no intention to be bound by any expressed or implied theory presented in the preceding background or in the following Description of Embodiments.

Reference will now be made in detail to various embodiments of the subject matter, examples of which are illustrated in the accompanying drawings. While various embodiments are discussed herein, it will be understood that they are not intended to limit to these embodiments. On the contrary, the presented embodiments are intended to cover alternatives, modifications and equivalents, which may be included within the spirit and scope the various embodiments as defined by the appended claims. Furthermore, in this Description of Embodiments, numerous specific details are set forth in order to provide a thorough understanding of embodiments of the present subject matter. However, embodiments may be practiced without these specific details. In other instances, well known methods, procedures, components, and circuits have not been described in detail as not to unnecessarily obscure aspects of the described embodiments.

Notation and Nomenclature

Some portions of the detailed descriptions which follow are presented in terms of procedures, logic blocks, processing and other symbolic representations of operations on data within an electrical device. These descriptions and representations are the means used by those skilled in the data processing arts to most effectively convey the substance of their work to others skilled in the art. In the present application, a procedure, logic block, process, or the like, is conceived to be one or more self-consistent procedures or instructions leading to a desired result. The procedures are those requiring physical manipulations of physical quantities. Usually, although not necessarily, these quantities take the form of acoustic (e.g., ultrasonic) signals capable of being transmitted and received by an electronic device and/or electrical or magnetic signals capable of being stored, transferred, combined, compared, and otherwise manipulated in an electrical device.

It should be borne in mind, however, that all of these and similar terms are to be associated with the appropriate physical quantities and are merely convenient labels applied to these quantities. Unless specifically stated otherwise as apparent from the following discussions, it is appreciated that throughout the description of embodiments, discussions utilizing terms such as "transmitting," "receiving," "sensing," "generating," "imaging," or the like, refer to the actions and processes of an electronic device such as an ultrasonic transducer or an array of ultrasonic transducers.

Embodiments described herein may be discussed in the general context of processor-executable instructions residing on some form of non-transitory processor-readable medium, such as program modules, executed by one or more computers or other devices for controlling operation of one or more dual layer ultrasonic transducer devices. Various techniques described herein may be implemented in hardware, software, firmware, or any combination thereof, unless specifically described as being implemented in a specific manner. Any features described as modules or components may also be implemented together in an integrated logic device or separately as discrete but interoperable logic devices. If implemented in software, the techniques may be realized at least in part by a non-transitory processor-readable storage medium comprising instructions that, when executed, perform one or more of the methods described herein. The non-transitory processor-readable data storage medium may form part of a computer program product, which may include packaging materials.

The non-transitory processor-readable storage medium may comprise random access memory (RAM) such as synchronous dynamic random access memory (SDRAM), read only memory (ROM), non-volatile random access memory (NVRAM), electrically erasable programmable read-only memory (EEPROM), FLASH memory, other known storage media, and the like. The techniques additionally, or alternatively, may be realized at least in part by a processor-readable communication medium that carries or communicates code in the form of instructions or data structures and that can be accessed, read, and/or executed by a computer or other processor.

Various embodiments described herein may be executed by one or more processors, such as one or more, sensor processing units (SPUs), host processor(s) or core(s) thereof, digital signal processors (DSPs), general purpose microprocessors, application specific integrated circuits (ASICs), application specific instruction set processors (ASIPs), field programmable gate arrays (FPGAs), a programmable logic controller (PLC), a complex programmable logic device (CPLD), a discrete gate or transistor logic, discrete hardware components, or any combination thereof designed to perform the functions described herein, or other equivalent integrated or discrete logic circuitry. The term "processor," as used herein may refer to any of the foregoing structures or any other structure suitable for implementation of the techniques described herein. As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Moreover, processors can exploit nano-scale architectures such as, but not limited to, molecular and quantum-dot based transistors, switches and gates, in order to optimize space usage or enhance performance of user equipment. A processor may also be implemented as a combination of computing processing units.

In addition, in some aspects, the functionality described herein may be provided within dedicated software modules or hardware modules configured as described herein. Also, the techniques could be fully implemented in one or more circuits or logic elements. A general purpose processor may be a microprocessor, but in the alternative, the processor may be any conventional processor, controller, microcontroller, or state machine. A processor may also be implemented as a combination of computing devices, e.g., a combination of an SPU and a microprocessor, a plurality of microprocessors, one or more microprocessors in conjunction with an SPU core, or any other such configuration.

Overview of Discussion

Discussion includes a description of an example single piezoelectric layer ultrasonic transducer, in accordance with various embodiments. Differential sensing using a single piezoelectric layer ultrasonic transducer, according to some embodiments, is then described. Example dual piezoelectric layer ultrasonic transducers, in accordance with various embodiments, are then described. Differential sensing using a dual piezoelectric layer ultrasonic transducer, according to some embodiments, is then described.

Embodiments described herein relate to ultrasonic transducer devices for differential sensing. In one embodiment, the ultrasonic transducer device includes a substrate, an edge support structure connected to the substrate, and a membrane connected to the edge support structure such that a cavity is defined between the membrane and the substrate and the membrane is configured to allow movement at ultrasonic frequencies. The membrane includes a structural layer, a piezoelectric layer having a first surface and a second surface, a first electrode placed on the first surface of the piezoelectric layer and located at the center of the membrane, a second electrode placed on the first surface of the piezoelectric layer, wherein the second electrode is a patterned electrode comprising more than one electrode components located at the edges of the membrane, and a third electrode placed on the second surface of the piezoelectric layer and electrically coupled to ground. In some embodiments, the ultrasonic transducer device further includes a fourth electrode between the edge support structure and the substrate, wherein the third electrode and fourth electrode are electrically coupled to operate as a ground electrode. In some embodiments, during a receive operation, the first electrode and the second electrode operate to provide differential receiving. In some embodiments, during a transmit operation, the first electrode and the second electrode are driven with waveforms having inverse potentials. In some embodiments, the first electrode and the second electrode include an optimized surface area to provide capacitance matching. In some embodiments, the position relative to the center of the membrane of the first and the second electrodes is optimized to provide amplitude and phase matching over a frequency range of interest.

According to some other embodiments, the ultrasonic transducer device includes a substrate, an edge support structure connected to the substrate, and a membrane connected to the edge support structure such that a cavity is defined between the membrane and the substrate and the membrane is configured to allow movement at ultrasonic frequencies. The membrane includes a first piezoelectric layer having a first surface and a second surface, a second piezoelectric layer having a first surface and a second surface, wherein the second surface of the first piezoelectric layer faces the first surface of the second piezoelectric layer, a buffer layer between the first piezoelectric layer and the second piezoelectric layer, a first electrode placed on the first surface of the first piezoelectric layer, a second electrode placed on the first surface of the second piezoelectric layer such that the second electrode is disposed between the second piezoelectric layer and the buffer layer, and a third electrode placed on the second surface of first piezoelectric layer, such that the third electrode is disposed between the first piezoelectric layer and the buffer layer. In some embodiments, the ultrasonic transducer device further includes a fourth electrode placed on the second surface of the second piezoelectric layer, wherein the third electrode and fourth electrode are electrically coupled to operate as a ground electrode. In some embodiments, during a receive operation, the first electrode and the second electrode operate to provide differential receiving. In some embodiments, during the transmit operation, the first electrode and the second electrode are driven with waveforms having inverse potentials. In some embodiments, the first electrode is a patterned electrode comprising more than one electrode components that are electrically coupled. In some embodiments, the second electrode is a patterned electrode comprising more than one electrode components that are electrically coupled. In some embodiments, the first electrode, the second electrode, and the third electrode include an optimized surface area to provide capacitance matching. In some embodiments, the position relative to the center of the membrane of the components of the first electrode is optimized to provide amplitude and phase matching over a frequency range of interest. In some embodiments, the position relative to the center of the membrane of the components of the second electrode is optimized to provide amplitude and phase matching over a frequency range of interest.

The described dual layer ultrasonic transducer device can be used for generation of acoustic signals or measurement of acoustically sensed data in various applications, such as, but not limited to, medical applications, security systems, biometric systems (e.g., fingerprint sensors and/or motion/gesture recognition sensors), mobile communication systems, industrial automation systems, consumer electronic devices, robotics, etc., for example, using multiple ultrasonic transducer devices operating collectively. In one embodiment, the ultrasonic transducer devices described herein can facilitate ultrasonic signal differential sensing. Moreover, embodiments describe herein provide a differential sensing component including a substrate including a two-dimensional (or one-dimensional) array of ultrasonic transducer devices.

Differential Receive at an Ultrasonic Transducer

Embodiments described herein ultrasonic transducers that are configured to provide for a differential receive operation. One or more embodiments are now described with reference to the drawings, wherein like reference numerals are used to refer to like elements throughout. In the following description, for purposes of explanation, numerous specific details are set forth in order to provide a thorough understanding of the various embodiments. It may be evident, however, that the various embodiments can be practiced without these specific details. In other instances, well-known structures and devices are shown in block diagram form in order to facilitate describing the embodiments in additional detail.

As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form. In addition, the word "coupled" is used herein to mean direct or indirect electrical or mechanical coupling. In addition, the word "example" is used herein to mean serving as an example, instance, or illustration.

FIG. 1A is a diagram illustrating an ultrasonic transducer device 100 with a single piezoelectric layer and receive (RX) electrodes on the same plane, according to some embodiments. In some embodiments, ultrasonic transducer device 100 is a piezoelectric micromachined ultrasonic transducer (PMUT) device. Ultrasonic transducer device 100 includes a membrane 110 attached to a surrounding edge support 105 and positioned over a substrate 140 to define a cavity 130. Ultrasonic transducer device 100 includes electrodes 122, 124 and 126. Electrode 126 is placed on the surface of the piezoelectric layer that overlies the cavity 130. Electrodes 122 and 124 are located on the same surface of piezoelectric layer 114 at the opposite side of cavity 130. Electrodes 124a and 124b are electrode components connected to the same terminal (collectively referred to as electrode 124) and operate as a single electrode. Edge support 105 may be made of electrically conducting materials, such as and without limitation, aluminum, molybdenum, or titanium. Edge support 105 may also be made of dielectric materials, such as silicon dioxide, silicon nitride or aluminum oxide that have electrical connections along the sides or in vias through edge support 105, for electrically coupling electrode 122, 124, or 126 to electrical wiring in substrate 140. In some embodiments, ultrasonic transducer device 100 also includes electrodes 128a and 128b placed between edge support 105 and substrate 140 that are electrode components connected to the same terminal (collectively referred to as electrode 128) and operate as a single electrode. For example, substrate 140 may include terminals for electrically coupling electrodes 122, 124, 126, and/or 128 to control circuitry.

In various embodiments, substrate 140 may include at least one of, and without limitation, silicon or silicon nitride. It should be appreciated that substrate 140 may include electrical wirings and connection, such as aluminum or copper. In one embodiment, substrate 140 includes a CMOS logic wafer bonded to edge support 105. Membrane 110 includes piezoelectric layer 114 and electrodes 122, 124, and 126, with electrodes 122 and 124 placed on the same side of piezoelectric layer 114 and electrode 126 located on the opposite side of piezoelectric layer 114 than electrodes 122 and 124, where electrode 126 is within cavity 130. In accordance with some embodiments, membrane 110 further includes structural layer 112 (e.g., a stiffening layer or a mechanical support layer) to mechanically stiffen membrane 110. In various embodiments, structural layer 112 may include at least one of, and without limitation, silicon, silicon oxide, silicon nitride, aluminum, molybdenum, titanium, etc.

Figure 1B:
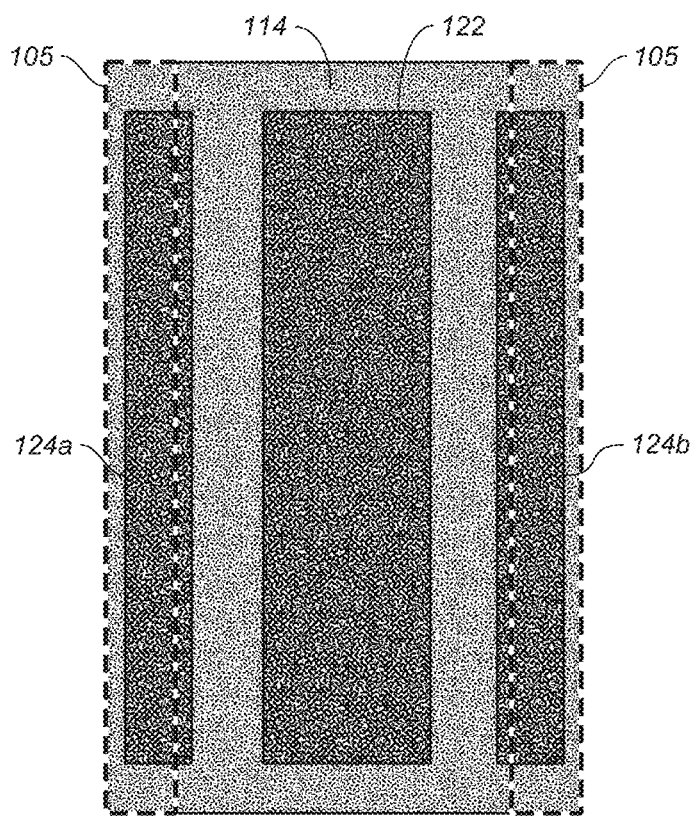
FIG. 1B is a diagram illustrating a view of a top surface of a piezoelectric layer of an ultrasonic transducer device showing the patterned receive (RX) electrodes, according to some embodiments.

FIG. 1B is a diagram illustrating a view of a top surface of piezoelectric layer 114 of ultrasonic transducer device 100 showing patterned electrodes 122 and 124, where electrode 124 includes electrode components 124a and 124b, according to some embodiments. As shown in FIG. 1B, electrode 122 is located at the center of the membrane, while electrode components 124a and 124b each partially overlie edge support position 106, where edge support position 106 identifies the relative location of edge support 105 under electrode components 124a and 124b.

With reference to FIGS. 1A and 1B, ultrasonic transducer device 100 is configured to provide differential receive due to the placement of electrodes 122 and 124, located on the same surface of piezoelectric layer 114, by exploiting a deflection mode of ultrasonic transducer device 100 in the frequency range of interest. Electrode 122 is disposed in a central region of ultrasonic transducer device 100, which is the region of maximum strain of ultrasonic transducer device 100, and electrode 124 is placed close to or over edge supports 105. Such placement of electrodes 122 and 124 provides for enhanced receive sensitivity. Furthermore, during a receive operation, the placement of electrodes 122 and 124 provides for the cancellation of correlated noise.

In order to design ultrasonic transducer device 100 for optimal differential sensing, sensitivities of received charges at electrodes 122 and 124 should match in terms of capacitance, amplitude, and phase. In accordance with some embodiments, capacitance matching is achieved by providing electrodes 122 and 124 having an optimized area. In accordance with some embodiments, amplitude and phase matching is achieved optimizing the relative position of electrodes 122 and 124, accounting for a deflection mode of the ultrasonic transducer device 100 in the frequency range of interest.

While embodiments described herein are directed toward a single layer ultrasonic transducer device including one piezoelectric layer, it should be appreciated that the principles described herein allow for the use of more than one piezoelectric layer, and that in some conceivable embodiments a multi-layer ultrasonic transducer device including more than one piezoelectric layer may be utilized. It should be appreciated that, in various embodiments, ultrasonic transducer device 100 is a microelectromechanical (MEMS) device. In accordance with various embodiments, piezoelectric layer 114 has thicknesses in the range of one to ten microns.

It should be appreciated that, ultrasonic transducer device 100 (and membrane 110) can be one of many types of geometric shapes (e.g., ring, circle, square, octagon, hexagon, etc.). For example, a sensing device may include an array of ultrasonic transducer devices 100. In some embodiments, ultrasonic transducer devices 100 can be of a shape that allows for close adjacent placement of ultrasonic transducer devices 100. In some embodiments, adjacent ultrasonic transducer devices 100 within an array may share edge support structures 105. In other embodiments, adjacent ultrasonic transducer devices 100 within an array are electrically and physically isolated from each other (e.g., separated by a gap).

It should be appreciated that in accordance with various embodiments, membrane 110 can also include other layers (not shown), such as an acoustic coupling layer. The acoustic coupling layer is for supporting transmission of acoustic signals, and, if present, is above membrane 110. It should be appreciated that acoustic coupling layer can include air, liquid, gel-like materials, or other materials for supporting transmission of acoustic signals.

In some embodiments, a plurality of ultrasonic transducer devices 100 are comprised within a two-dimensional (or one-dimensional) array of ultrasonic transducer devices 100. In such embodiments, the array of ultrasonic transducer devices 100 may be coupled to a platen layer above an acoustic coupling layer for containing the acoustic coupling layer and providing a contact surface for a finger or other sensed object with the array of ultrasonic transducer devices 100. It should be appreciated that, in various embodiments, the acoustic coupling layer provides a contact surface, such that a platen layer is optional. It should be appreciated that the contact surface can be flat or of a varying thickness (e.g., curved).

The described ultrasonic transducer device 100 is capable of generating and receiving ultrasonic signals. An object in a path of the generated ultrasonic signals can create a disturbance (e.g., changes in frequency or phase, reflection signal, echoes, etc.) that can then be sensed. The interference can be analyzed to determine physical parameters such as (but not limited to) distance, density and/or speed of the object. As an example, the ultrasonic transducer device 100 can be utilized in various applications, such as, but not limited to, fingerprint or physiologic sensors suitable for wireless devices, industrial systems, automotive systems, robotics, telecommunications, security, medical devices, etc. For example, the ultrasonic transducer device 100 can be part of a sensor array comprising a plurality of ultrasonic transducers deposited on a wafer, along with various logic, control and communication electronics. A sensor array may comprise homogenous or identical ultrasonic transducer devices 100, or a number of different or heterogonous device structures.

In various embodiments, the ultrasonic transducer device 100 employs piezoelectric layer 114, comprised of materials such as, but not limited to, aluminum nitride (AlN), scandium doped aluminum nitride (ScAlN), lead zirconate titanate (PZT), quartz, polyvinylidene fluoride (PVDF), and/or zinc oxide, to facilitate both acoustic signal production (transmitting) and sensing (receiving). Piezoelectric layer 114 can generate electric charges under mechanical stress and conversely experience a mechanical strain in the presence of an electric field. For example, piezoelectric layer 114 can sense mechanical vibrations caused by an ultrasonic signal and produce an electrical charge at the frequency (e.g., ultrasonic frequency) of the vibrations. Additionally, piezoelectric layer 114 can generate an ultrasonic wave by vibrating in an oscillatory fashion that might be at the same frequency (e.g., ultrasonic frequency) as an input current generated by an alternating current (AC) voltage applied across the piezoelectric layer 114. It should be appreciated that piezoelectric layer 114 can include almost any material (or combination of materials) that exhibits piezoelectric properties. The polarization is directly proportional to the applied stress and is direction dependent so that compressive and tensile stresses results in electric fields of opposite polarizations.

Further, ultrasonic transducer device 100 comprises electrodes 122, 124, 126, and 128 that supply and/or collect the electrical charge to/from piezoelectric layer 114. Electrodes 122, 124, 126, and 128 can be connected to substrate 140 or the underlying circuitry via one or more terminals on substrate 140. Depending on the mode of operation, two or more electrodes may share a single terminal. It should be appreciated that electrodes 122, 124, 126, and 128 are patterned electrodes (e.g., a patterned layer). As an example, electrodes 122, 124, 126, and 128 can be comprised of almost any metal layers, such as, but not limited to, aluminum (Al), titanium (Ti), Molybdenum (Mo), etc.

In accordance with various embodiments, electrodes 122, 124, and/or 126 can be patterned in particular shapes (e.g., ring, circle, square, octagon, hexagon, etc.) that are defined accordingly to the geometrical shape of ultrasonic transducer device 100 (and of membrane 110) and/or to a selected deflection mode of the transducer in the frequency range of interest. Electrodes 122 and 126 are placed at a maximum strain area of the membrane 110 (e.g., around the mid-point of membrane 110) and electrodes 124*a* and 124*b* are placed close to and/or over edge support 105. In some embodiments, the electrode 126 can be routed along edge support 105. For example, when an acoustic wave hits ultrasonic transducer device 100, membrane 110 will deform and move out of plane. The deflection results in the generation of electric charge.

In some embodiments, electrodes 122 and 124 are coupled to different terminals and operate as separate electrodes, where electrodes 126 and 128 are coupled to ground (GND) or other potential.

Figure 2:
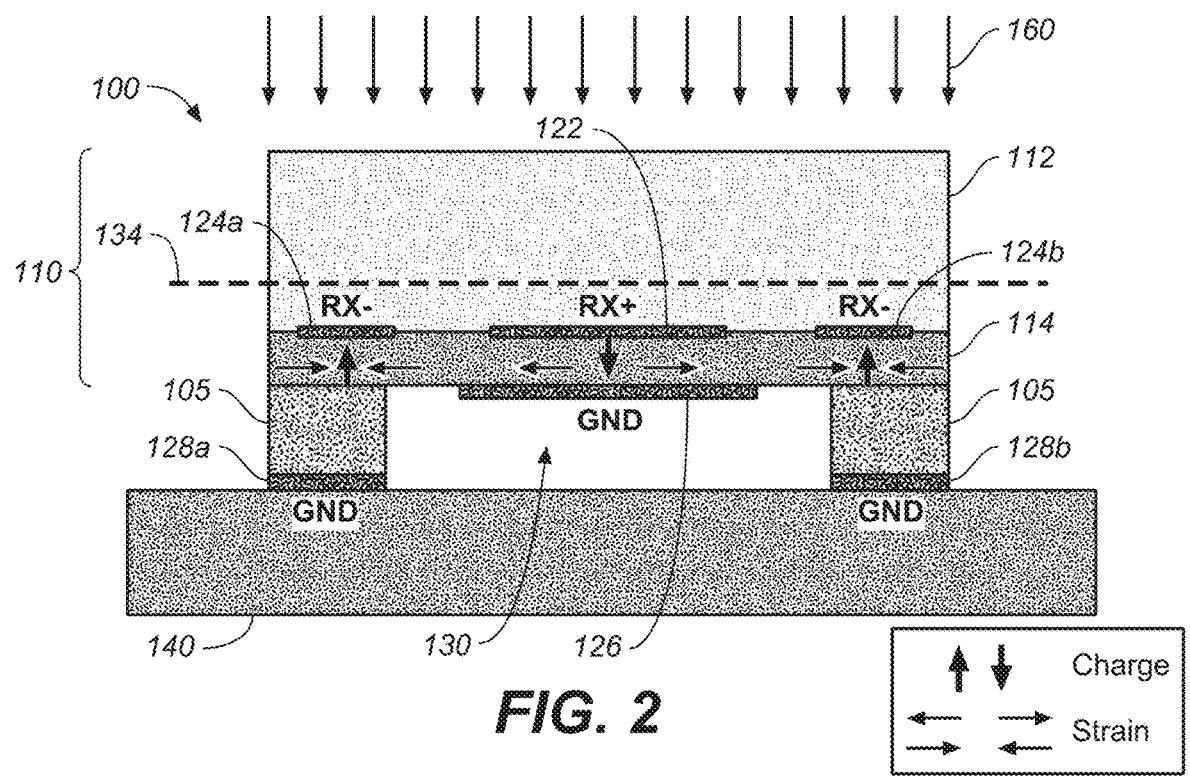
FIG. 2 is a diagram illustrating an example of differential receive operation of an ultrasonic transducer device with a single piezoelectric layer and receive (RX) electrodes placed on the same plane, according to some embodiments.

FIG. 2 is a diagram illustrating an example differential receive operation of an ultrasonic transducer device 100 with electrodes 122 and 124 placed on the same surface of the piezoelectric layer 114, according to some embodiments. Differential receive is achieved exploiting a deflection mode of the ultrasonic transducer device 100 in the frequency range of interest. Electrode 122, denoted in FIG. 2 as RX+, is disposed in a central region of ultrasonic transducer device 100, which is the region of maximum strain of ultrasonic transducer device 100, and electrodes 124a and 124b, denoted in FIG. 2 as RX−, are placed close to or over edge support 105, in the region where the strain has an opposite sign with respect to the center of the membrane 110 accordingly to the selected deflection mode of ultrasonic transducer device 100. Neutral axis 134 identifies the neutral position of flexural strain of ultrasonic transducer device 100.

During the differential receive operation, the deflection of membrane 110 is induced by the incoming pressure (illustrated as arrows 160), causing charge to be collected at electrode 122 and electrode 124. Exploiting a selected deflection mode of the ultrasonic transducer device 100 in the frequency range of interest, electrode 122 and electrode 124, denoted in FIG. 2 as RX+ and RX− respectively, are charged in (nearly) anti-phase. In some embodiments, electrodes 122 and 124 are coupled to different terminals and operate as separate electrodes. In accordance with various embodiments, electrodes 122 and 124 have an optimized area to provide for capacitance matching. In accordance with some embodiments, the relative position of electrodes 122 and 124 is optimized to provide for amplitude and phase matching. Electrodes 126 and 128 are coupled to ground (GND) or other potential.

For example, as the membrane flexes during receive, strain induced charges are generated across piezoelectric layer 114. Due to the different polarity of the charges induced as a function of the direction of the bending strains, electrodes 122 and 124 can be designed according to the shape and location of these strains to capture the differential signals. For the differential receive mode, electrodes 122 and 124 used for the receive operation can be arranged such that electrodes 122 and 124 contact portions of piezoelectric layer 114 with nearly anti-phase stress. Taking as differential signal across electrodes 122 and 124 can help increase the receive signal. Electrodes 122 and 124 may be connected to different inputs of a differential amplifier in the sensing circuit.

Figure 3A:
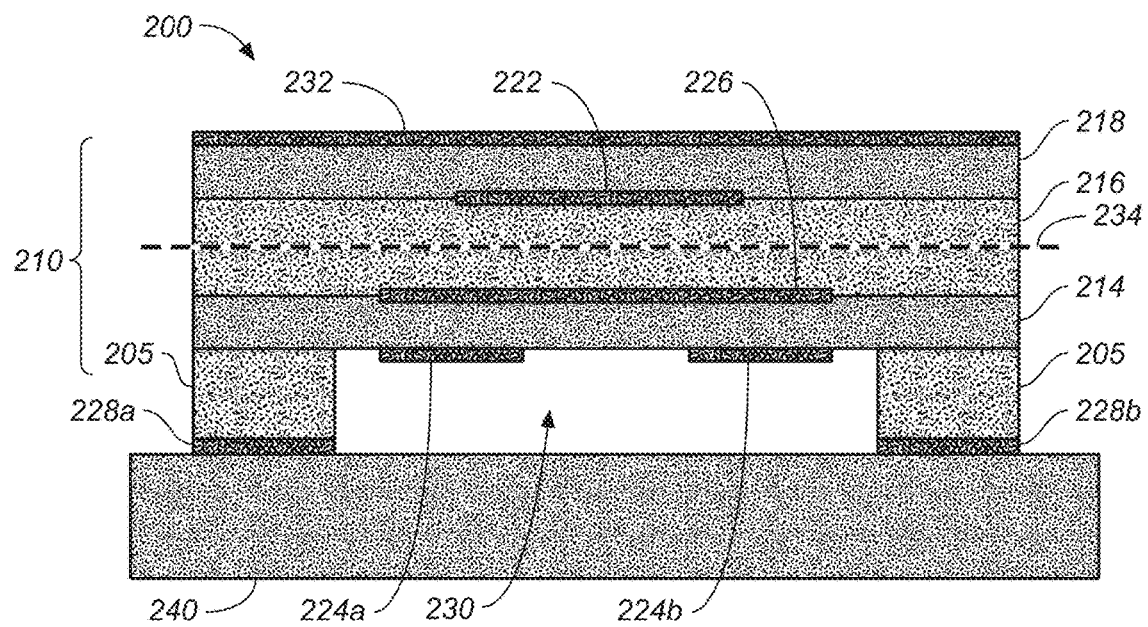
FIG. 3A is a diagram illustrating a side view of an ultrasonic transducer device with two piezoelectric layers and a buffer layer between them, according to some embodiments.

FIG. 3A is a diagram illustrating an ultrasonic transducer device 200 with two piezoelectric layers 214 and 218 and a buffer layer 216 between them, according to some embodiments. In some embodiments, ultrasonic transducer device 200 is a PMUT device. Dual layer ultrasonic transducer device 200 includes a membrane 210 attached to a surrounding edge support 205 and positioned over a substrate 240 to define a cavity 230. Ultrasonic transducer device 200 includes electrodes 222, 224 and 226. Electrodes 224a and 224b are electrode components connected to the same terminal (collectively referred to as electrode 224) and operate as a single electrode. Electrodes 224 and 226 are patterned electrodes placed at the opposite sides of the bottom piezoelectric layer 214, with electrode 224 overlying the cavity 230. Electrode 222 is a patterned electrode located at the bottom surface of the top piezoelectric layer 218. Edge support 205 may be made of electrically conducting materials, such as and without limitation, aluminum, molybdenum, or titanium. Edge support 205 may also be made of dielectric materials, such as silicon dioxide, silicon nitride or aluminum oxide that have electrical connections along the sides or in vias through edge support 205, for electrically coupling electrode 222, 224, or 226 to electrical wiring in substrate 240. Ultrasonic transducer device 200 also includes electrodes 228a and 228b between edge supports 205 and substrate 240 that are electrode components connected to the same terminal (collectively referred to as electrode 228) and operate as a single electrode. In some embodiments, ultrasonic transducer device 200 also includes ground electrode 232 disposed over piezoelectric layer 218. For example, substrate 240 may include terminals for electrically coupling electrodes 222, 224, 226, 228, and/or 232 to control circuitry.

In various embodiments, substrate 240 may include at least one of, and without limitation, silicon or silicon nitride. It should be appreciated that substrate 240 may include electrical wirings and connection, such as aluminum or copper. In one embodiment, substrate 240 includes a CMOS logic wafer bonded to edge support 205. Membrane 210 includes piezoelectric layers 214 and 218, buffer layer 216, and electrodes 222, 224, and 226. Buffer layer 216 is positioned between piezoelectric layers 214 and 218. Electrode 222 is between piezoelectric layer 218 and buffer layer 216, electrode 226 is between buffer layer 216 and piezoelectric layer 214, and electrode 224 is on the opposite side of piezoelectric layer 214 than electrodes 226, where electrode 224 is within cavity 230. While embodiments described herein are directed toward a dual layer ultrasonic transducer device 200 including two piezoelectric layers, it should be appreciated that the principles described herein allow for the use of more than two piezoelectric layers, and that in some conceivable embodiments a multi-layer ultrasonic transducer device including more than two piezoelectric layers may be utilized. It should be appreciated that, in various embodiments, dual ultrasonic transducer device 200 is a microelectromechanical (MEMS) device.

FIGS. 3B and 3C are diagrams illustrating views of bottom surfaces of piezoelectric layers 218 and 214, respectively, of ultrasonic transducer device 200 showing the electrodes 222 and 224, where electrode 224 includes electrode components 224a and 224b, according to some embodiments. Electrodes 222 and 224 are coupled to different terminals and operate as separate electrodes. As shown in FIG. 3B, electrode 222 is positioned towards the middle of the bottom surface of piezoelectric layer 218. As shown in FIG. 3C, electrode components 224a and 224b are positioned between a midpoint of piezoelectric layer 214 and edge support position 206, where edge support position 206 identifies the relative location of edge support 205.

With reference to FIGS. 3A-3C, ultrasonic transducer device 200 is configured to provide differential receive in part due to the placement of electrodes 222 and 224 on opposites sides of neutral axis 234 of ultrasonic transducer device 200 to collect the charges due to the deformation induced by the incoming pressure and read voltages in anti-phase. Electrodes 222 and 224 are disposed in a central region of ultrasonic transducer device 200, which is the region of maximum strain of ultrasonic transducer device 200. Such placement of electrodes 222 and 224 provides for enhanced receive sensitivity. Furthermore, during a receive operation, the placement of electrodes 222 and 224 provides for the cancellation of correlated noise. In some embodiments, placement of electrode components 224a and 224b allows for the placement of another electrode (e.g., a transmit electrode) between electrode components 224a and 224b. In other embodiments, placement of electrode components 224a and 224b allows for the matching of receive signal sensitivities.

In order to design ultrasonic transducer device 200 for optimal differential sensing, sensitivities of received charges at electrodes 222 and 224 should match in terms of capacitance, amplitude, and phase. In accordance with various embodiments, the surface area of electrodes 222 and 224 is optimized to provide capacitance, amplitude and phase matching. In accordance with various embodiments, the distance of electrodes 224a and 224b with respect to the center of the membrane is optimized to achieve amplitude and phase matching.

It should be appreciated that dual layer ultrasonic transducer device 200 (and membrane 210) can be one of many types of geometric shapes (e.g., ring, circle, square, octagon, hexagon, etc.). For example, a sensing device may include an array of dual layer ultrasonic transducer devices 200. In some embodiments, the dual layer ultrasonic transducer devices 200 can be of a shape that allows for close adjacent placement of dual layer ultrasonic transducer devices 200. In some embodiments, adjacent dual layer ultrasonic transducer devices 200 within an array may share edge support structures 205. In other embodiments, adjacent dual layer ultrasonic transducer devices 200 within an array are electrically and physically isolated from each other (e.g., separated by a gap).

It should be appreciated that in accordance with various embodiments, membrane 210 can also include other layers (not shown), such a mechanical support layer, e.g., a structural layer or a stiffening layer, and an acoustic coupling layer. The mechanical support layer is configured to mechanically stiffen the layers of membrane 210. The mechanical support layer can be above or below membrane 210. In various embodiments, the mechanical support layer may include at least one of, and without limitation, silicon, silicon oxide, silicon nitride, aluminum, molybdenum, titanium, etc. The acoustic coupling layer is for supporting transmission of acoustic signals, and, if present, is above membrane 210. It should be appreciated that acoustic coupling layer can include air, liquid, gel-like materials, or other materials for supporting transmission of acoustic signals.

In some embodiments, a plurality of dual layer ultrasonic transducer devices 200 are comprised within a two-dimensional (or one-dimensional) array of dual layer ultrasonic transducer devices. In such embodiments, the array of dual layer ultrasonic transducer devices 200 may be coupled to a platen layer above an acoustic coupling layer for containing the acoustic coupling layer and providing a contact surface for a finger or other sensed object with the array of dual layer ultrasonic transducer devices 200. It should be appreciated that, in various embodiments, the acoustic coupling layer provides a contact surface, such that a platen layer is optional. It should be appreciated that the contact surface can be flat or of a varying thickness (e.g., curved).

The described dual layer ultrasonic transducer device 200 is capable of generating and receiving ultrasonic signals. An object in a path of the generated ultrasonic signals can create a disturbance (e.g., changes in frequency or phase, reflection signal, echoes, etc.) that can then be sensed. The interference can be analyzed to determine physical parameters such as (but not limited to) distance, density and/or speed of the object. As an example, the dual layer ultrasonic transducer device 200 can be utilized in various applications, such as, but not limited to, fingerprint or physiologic sensors suitable for wireless devices, industrial systems, automotive systems, robotics, telecommunications, security, medical devices, etc. For example, the dual layer ultrasonic transducer device 200 can be part of a sensor array comprising a plurality of ultrasonic transducers deposited on a wafer, along with various logic, control and communication electronics. A sensor array may comprise homogenous or identical dual layer ultrasonic transducer devices 200, or a number of different or heterogonous device structures.

In various embodiments, the dual layer ultrasonic transducer device 200 employs piezoelectric layers 214 and 218, comprised of materials such as, but not limited to, aluminum nitride (AlN), scandium doped aluminum nitride (ScAlN), lead zirconate titanate (PZT), quartz, polyvinylidene fluoride (PVDF), and/or zinc oxide, to facilitate both acoustic signal production (transmitting) and sensing (receiving). It should be appreciated that piezoelectric layers 214 and 218 can be comprised of the same material or different materials. The piezoelectric layers 214 and/or 218 can generate electric charges under mechanical stress and conversely experience a mechanical strain in the presence of an electric field. For example, piezoelectric layers 214 and/or 218 can sense mechanical vibrations caused by an ultrasonic signal and produce an electrical charge at the frequency (e.g., ultrasonic frequency) of the vibrations. Additionally, piezoelectric layers 214 and/or 218 can generate an ultrasonic wave by vibrating in an oscillatory fashion that might be at the same frequency (e.g., ultrasonic frequency) as an input current generated by an alternating current (AC) voltage applied across the piezoelectric layers 214 and/or 218. It should be appreciated that piezoelectric layers 214 and 218 can include almost any material (or combination of materials) that exhibits piezoelectric properties. The polarization is directly proportional to the applied stress and is direction dependent so that compressive and tensile stresses results in electric fields of opposite polarizations.

Buffer layer 216 separates piezoelectric layers 214 and 218. Buffer layer 216 can be comprised of materials such as, but not limited to, silicon, silicon oxide, polysilicon, silicon nitride, or any non-conducting oxide layer (or stacks of layers). Moreover, it should be appreciated that the buffer material can be application specific, e.g., selected based on a desired frequency of operation of dual layer ultrasonic transducer device 200. For example, buffer layer 216 can be a metal. It should be appreciated that the stiffer the material of buffer layer 216, the higher the frequency.

Buffer layer 216 allows for improved tuning of the transmit and receive operations, by enhancing the performance of the transmit and receive operations. The frequency can be tuned according to thickness of buffer layer 216 so as to optimize the thicknesses of piezoelectric layers 214 and 218 and/or to improve the figure of merit (FOM) of dual layer ultrasonic transducer device 200. Moreover, the neutral axis can be designed to not be in the middle of membrane 210 so as to achieve a better FOM. Buffer layer 216 also supports tuning of the thicknesses and materials of piezoelectric layers 214 and 218.

Further, dual layer ultrasonic transducer device 200 comprises electrodes 222, 224, 226, 228, and 232 that supply and/or collect the electrical charge to/from piezoelectric layers 214 and 218. Electrodes 222, 224, 226, 228, and 232 can be connected to substrate 240 or the underlying circuitry via one or more terminals on substrate 240. Depending on the mode of operation, two or more electrodes may share a single terminal. It should be appreciated that electrodes 222, 224, 226, and 228 are patterned electrodes and electrode 232 can be a patterned or continuous electrode (e.g., in a continuous layer and/or a patterned layer). As an example, electrodes 222, 224, 226, 228, and 232 can be comprised of almost any metal layers, such as, but not limited to, aluminum (Al), titanium (Ti), Molybdenum (Mo), etc.

In accordance with various embodiments, electrodes 222, 224, and/or 226 can be patterned in particular shapes (e.g., ring, circle, square, octagon, hexagon, etc.) that are defined accordingly to the geometrical shape of ultrasonic transducer device 200 (and of membrane 210) and/or to a deflection mode of the transducer in the frequency range of interest. Electrodes 222, 224, and 226 can be placed at a maximum strain area of the membrane 210 or placed close to edge support 205. Furthermore, in one example, electrode 232 can be formed as a continuous layer providing a ground plane or other potential. In another example, electrode 232 can be formed as a continuous layer in contact with an additional mechanical support layer (not shown), which can be formed from silicon or other suitable mechanical stiffening material. In still other embodiments, the electrode 224 can be routed along edge support 205. For example, when an acoustic wave hits ultrasonic transducer device 200, membrane 210 will deform and move out of plane. The deflection results in the generation of electric charge.

In some embodiments, electrodes 222 and 224 are coupled to different terminals and operate as separate electrodes, where electrodes 226, 228, and 232 are coupled to ground (GND) or other potential.

Figure 4:
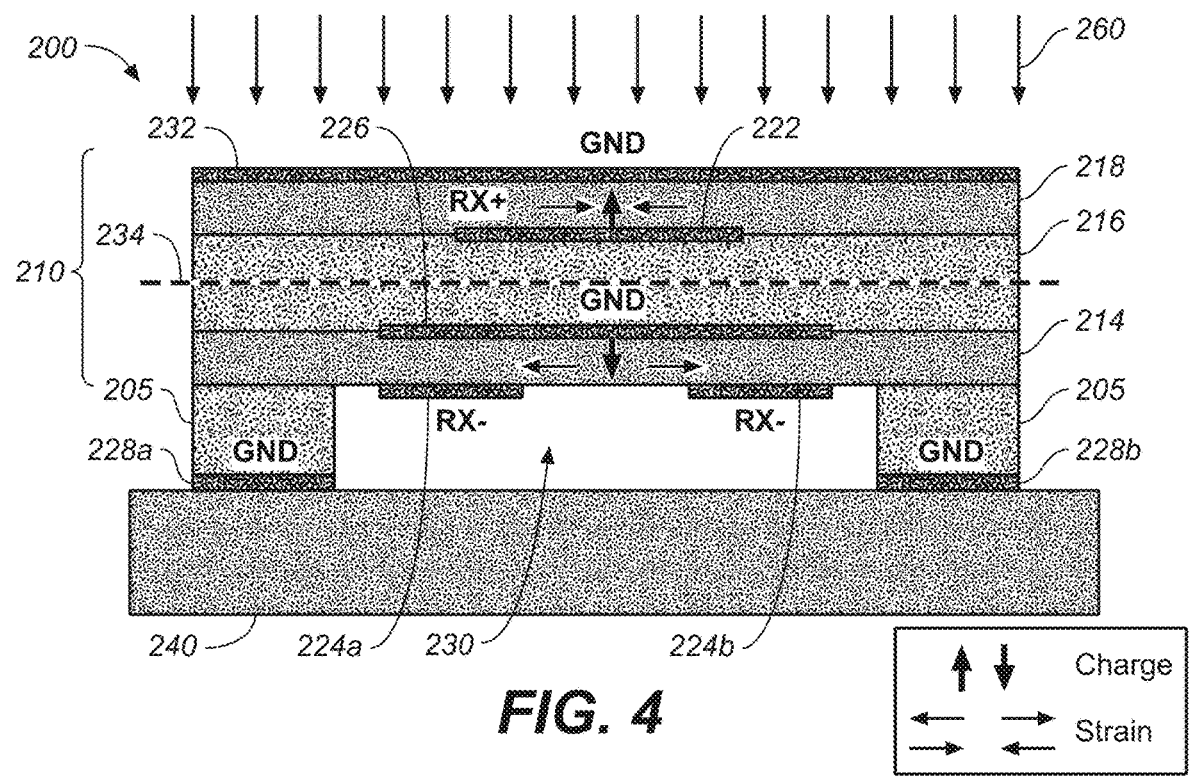
FIG. 4 is a diagram illustrating an example of differential receive operation of a dual piezoelectric layer ultrasonic transducer device, according to some embodiments.

FIG. 4 is a diagram illustrating an example of differential receive operation of a dual layer ultrasonic transducer device 200, according to some embodiments. Electrodes 222 and 224 are disposed in a central region of ultrasonic transducer device 200, which is the region of maximum strain of ultrasonic transducer device 200. Electrode 224 is characterized by a larger mechanical leverage from neutral axis 234 than electrode 222. In some embodiments, to account for the difference in mechanical leverage, the performance of electrode 224 should be impacted by increasing the distance of electrodes 224a and 224b from the point of maximum flexural strain of membrane 210, allowing for amplitude and phase matching of the received charges.

During the differential receive operation, the deformation of membrane 210 is induced by the incoming pressure (illustrated as arrows 260), causing charge to be collected at electrode 222 and electrode 224. In some embodiments, electrodes 222 and 224 are coupled to different terminals and operate as separate electrodes. In accordance with various embodiments, electrodes 222 and 224 have an optimized area to provide for capacitance matching. Electrodes 226, 228, and 232 are coupled to ground (GND) or other potential. In some embodiments, capacitance matching is achieved by designing electrode 226 of a sufficient size.

For example, as the membrane flexes during receive, strain induced charges are generated across piezoelectric layers 214 and 218. Due to the different polarity of the charges induced as a function of the direction of the bending strains, electrodes 222 and 224 can be designed according to the shape and location of these strains to capture the differential signals. For the differential receive mode, electrodes 222 and 224 used for the receive operation can be arranged such that electrodes 222 and 224 contact portions of piezoelectric layers 214 and 218 with anti-phase stress. Taking as differential signal across electrodes 222 and 224 can help increase the receive signal. Electrodes 222 and 224 may be connected to different inputs of a differential amplifier in the sensing circuit.

Figure 5A:
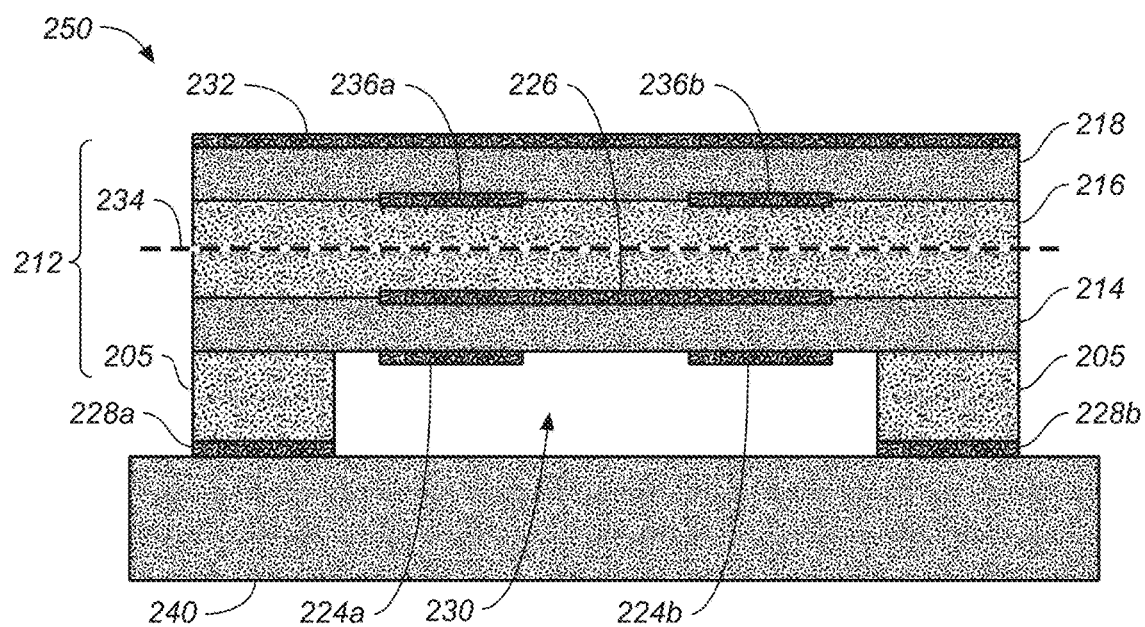
FIG. 5A is a diagram illustrating a side view of an ultrasonic transducer device with two piezoelectric layers and a buffer layer between them, according to other embodiments.

FIG. 5A is a diagram illustrating a dual layer ultrasonic transducer device 250 having two piezoelectric layers 214 and 218 and a buffer layer 216 between them, according to other embodiments. In some embodiments, ultrasonic transducer device 250 is a PMUT device. Dual piezoelectric layer ultrasonic transducer device 250 operates in a similar manner, and includes the same configuration, as dual piezoelectric layer ultrasonic transducer device 200 of FIG. 3A, apart from the explicit use of electrodes 236a and 236b (collectively referred to as electrode 236) in lieu of electrode 222 of FIG. 3A.

Dual piezoelectric layer ultrasonic transducer device 250 includes a membrane 212 attached to a surrounding edge support 205 and positioned over a substrate 240 to define a cavity 230. Ultrasonic transducer device 200 includes electrodes 224, 226 and 236. Electrodes 224 and 226 are patterned electrodes placed at the opposite sides of the bottom piezoelectric layer 214, with electrode 236 overlying the cavity 230. Electrode 236 is a patterned electrode located at the bottom surface of the top piezoelectric layer 218. Electrodes 224a and 224b are electrode components connected to the same terminal (collectively referred to as electrode 224) and operate as a single electrode. Electrodes 236a and 236b are electrode components connected to the same terminal (collectively referred to as electrode 236) and operate as a single electrode. In some embodiments, ultrasound transducer device 250 further includes electrode 228 placed between edge support 205 and substrate 240 and/or electrode 232 disposed over piezoelectric layer 218.

FIGS. 5B and 5C are diagrams illustrating views of bottom surfaces of piezoelectric layers 218 and 214, respectively, of ultrasonic transducer device 250 showing the electrodes 236 and 224, where electrode 236 includes electrode components 236a and 236b and where electrode 224 includes electrode components 224a and 224b, according to some embodiments. As shown in FIG. 5B, electrode components 236a and 236b are positioned between a midpoint of piezoelectric layer 218 and edge support position 206, where edge support position 206 identifies the relative location of edge support 205. As shown in FIG. 5C, electrode components 224a and 224b are positioned between a midpoint of piezoelectric layer 214 and edge support position 206. In some embodiments, placement of electrode components 224a and 224b and/or the placement of electrode components 236a and 236b allows for the placement of another electrode (e.g., a transmit electrode) between electrode components 224a and 224b and/or electrode components 236a and 236b. In other embodiments, placement of electrode components 224a and 224b and/or the placement of electrode components 236a and 236b allows for the amplitude and phase matching of receive signal sensitivities.

With reference to FIGS. 5A-5C, edge support 205 may be made of electrically conducting materials, such as and without limitation, aluminum, molybdenum, or titanium. Edge support 205 may also be made of dielectric materials, such as silicon dioxide, silicon nitride or aluminum oxide that have electrical connections along the sides or in vias through edge support 205, for electrically coupling electrode 224, 226, or 236 to electrical wiring in substrate 240. Ultrasonic transducer device 250 also includes electrodes 228a and 228b between edge support 205 and substrate 240 that are electrode components connected to the same terminal (collectively referred to as electrode 228) and operate as a single electrode. In some embodiments, ultrasonic transducer device 250 also includes electrode 232 disposed over piezoelectric layer 218. For example, substrate 240 may include terminals for electrically coupling electrodes 224, 226, 228, 232, and/or 236 to control circuitry.

Membrane 212 includes piezoelectric layers 214 and 218, buffer layer 216, and electrodes 224, 226, and 236. Buffer layer 216 is positioned between piezoelectric layers 214 and 218. Electrode 236 is between piezoelectric layers 218 and buffer layer 216, electrode 226 is between buffer layer 216 and piezoelectric layer 214, and electrode 224 is on the opposite side of piezoelectric layer 214 than electrodes 226, where electrode 224 is within cavity 230.

Ultrasonic transducer device 250 is configured to provide differential receive in part due to the placement of electrodes 224 and 236 on the opposites sides of the neutral axis 234 of ultrasonic transducer device 250 to collect the charges due to the deformation induced by the incoming pressure and read voltages in anti-phase. Electrodes 224 and 236 are disposed in a central region of ultrasonic transducer device 250, which is the region of maximum strain of ultrasonic transducer device 250. Such placement of electrodes 224 and 236 provides for enhanced receive sensitivity. Furthermore, during a receive operation, the placement of electrodes 224 and 236 provides for the cancellation of correlated noise.

In order to design ultrasonic transducer device 250 for optimal differential sensing, sensitivities of received charges at electrodes 224 and 236 should match in terms of capacitance, amplitude, and phase. In accordance with various embodiments, the surface area of electrodes 224 and 236 is optimized to provide capacitance, amplitude and phase matching. In accordance with various embodiments, the position of electrodes 224a and 224b and/or electrodes 236a and 236b with respect to the center of the membrane 212 is optimized to achieve amplitude and phase matching of the receive signals.

Further, dual piezoelectric layer ultrasonic transducer device 250 comprises electrodes 224, 226, 228, 232, and 236 that supply and/or collect the electrical charge to/from piezoelectric layers 214 and 218. Electrodes 224, 226, 228, 232, and 236 can be connected to substrate 240 or the underlying circuitry via one or more terminals on substrate 240. Depending on the mode of operation, two or more electrodes may share a single terminal. It should be appreciated that electrodes 224, 226, 228, and 236 are patterned electrodes and electrode 232 can be a patterned or continuous electrode (e.g., in a continuous layer and/or a patterned layer). As an example, electrodes 224, 226, 228, 232, and 236 can be comprised of almost any metal layers, such as, but not limited to, aluminum (Al), titanium (Ti), Molybdenum (Mo), etc.

In accordance with various embodiments, electrodes 224, 226, and/or 236 can be patterned in particular shapes (e.g., ring, circle, square, octagon, hexagon, etc.) that are defined accordingly to the geometrical shape of ultrasonic transducer device 250 (and of membrane 212) and/or to a deflection mode of the transducer in the frequency range of interest. Electrodes 224, 226, and 236 can be placed at a maximum strain area of the membrane 212 or placed close to edge support 205. Furthermore, in one example, electrode 232 can be formed as a continuous layer providing a ground plane or other potential. In another example, electrode 232 can be formed as a continuous layer in contact with a mechanical support layer (not shown), which can be formed from silicon or other suitable mechanical stiffening material. In still other embodiments, the electrode 224 can be routed along edge support 205. For example, when an acoustic wave hits ultrasonic transducer device 250, membrane 212 will deform and move out of plane. The deflection results in the generation of electric charge.

In some embodiments, electrodes 224 and 236 are coupled to different terminals and operate as separate electrodes, where electrodes 226, 228, and 232 are coupled to ground (GND) or other potential.

Figure 6:
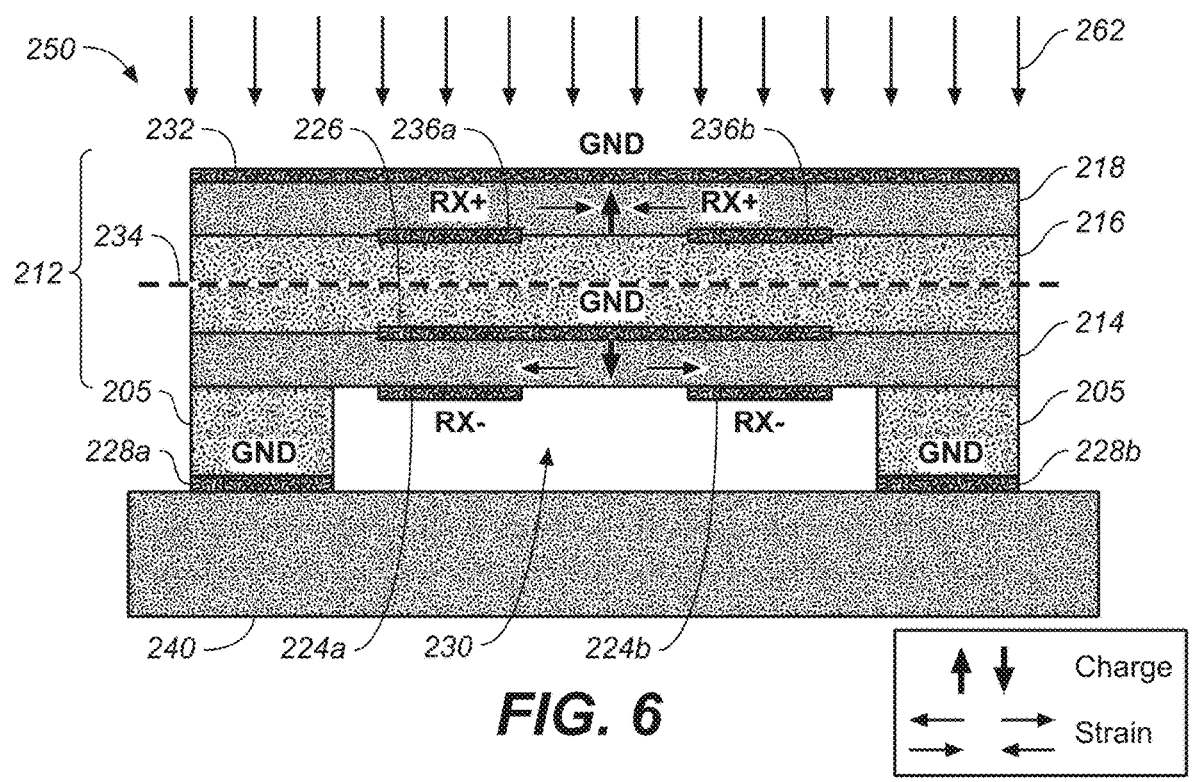
FIG. 6 is a diagram illustrating an example differential receive operation of a dual piezoelectric layer ultrasonic transducer device, according to other embodiments.

FIG. 6 is a diagram illustrating an example differential receive operation of a dual layer ultrasonic transducer device 250, according to other embodiments. Electrodes 224 and 236 are disposed in a central region of ultrasonic transducer device 250, which is the region of maximum strain of ultrasonic transducer device 250. Electrode 224 is characterized by a larger mechanical leverage from neutral axis 234 than electrode 236. In some embodiments, to account for the difference in mechanical leverage, the performance of electrode 224 should be impacted by increasing the distance of electrode 224 from the point of maximum flexural strain of membrane 212.

During the differential receive operation, the deformation of membrane 212 is induced by the incoming pressure (illustrated as arrows 262), causing charge to be collected at electrode 224 and electrode 236. In some embodiments, electrodes 224 and 236 are coupled to different terminals and operate as separate electrodes. In accordance with various embodiments, electrodes 224 and 236 have an optimized area and are located at an optimized distance from the mid-point of the membrane 212 to provide for capacitance, amplitude and phase matching. Electrodes 226, 228, and 232 are coupled to ground (GND) or other potential. In some embodiments, capacitance matching is achieved by designing electrode 226 of a sufficient size.

For example, as the membrane flexes during receive, strain induced charges are generated across piezoelectric layers 214 and 218. Due to the different polarity of the charges induced as a function of the direction of the bending strains, electrodes 224 and 236 can be designed according to the shape and location of these strains to capture the differential signals. For the differential receive mode, electrodes 224 and 236 used for the receive operation can be arranged such that electrodes 224 and 236 contact portions of piezoelectric layers 214 and 218 with anti-phase stress. Taking as differential signal across electrodes 224 and 236 can help increase the receive signal. Electrodes 224 and 236 may be connected to different inputs of a differential amplifier in the sensing circuit.

What has been described above includes examples of the subject disclosure. It is, of course, not possible to describe every conceivable combination of components or methodologies for purposes of describing the subject matter, but it is to be appreciated that many further combinations and permutations of the subject disclosure are possible. Accordingly, the claimed subject matter is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated examples of the claimed subject matter.

The aforementioned systems and components have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components. Any components described herein may also interact with one or more other components not specifically described herein.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

Thus, the embodiments and examples set forth herein were presented in order to best explain various selected embodiments of the present invention and its particular application and to thereby enable those skilled in the art to make and use embodiments of the invention. However, those skilled in the art will recognize that the foregoing description and examples have been presented for the purposes of illustration and example only. The description as set forth is not intended to be exhaustive or to limit the embodiments of the invention to the precise form disclosed.

What is claimed is:

1. An ultrasonic transducer device comprising:
   a substrate;
   an edge support structure connected to the substrate; and
   a membrane connected to the edge support structure such that a cavity is defined between the membrane and the substrate, the membrane configured to allow movement at ultrasonic frequencies, the membrane comprising:
   a structural layer;
   a piezoelectric layer having a first surface and a second surface;
   a first electrode placed on the first surface of the piezoelectric layer, wherein the first electrode is located at a center of the membrane;
   a second electrode placed on the first surface of the piezoelectric layer, wherein the second electrode is a patterned electrode comprising more than one electrode components located at an edge of the membrane; and
   a third electrode placed on the second surface of the piezoelectric layer;
   wherein the first electrode and the second electrode are operable during a transmit operation and a receive operation, and wherein, during the receive operation, the first electrode and the second electrode operate to provide differential receiving and the third electrode is coupled to ground.

2. The ultrasonic transducer device of claim 1, wherein, during the transmit operation, the first electrode and the second electrode are driven with waveforms having inverse potentials.

3. The ultrasonic transducer device of claim 1, wherein, during the transmit operation, the first electrode and the second electrode are driven with waveforms having inverse potentials and the third electrode is coupled to ground.

4. The ultrasonic transducer device of claim 1, wherein the first surface is at an opposite side of the cavity and the second surface overlies the cavity.

5. The ultrasonic transducer device of claim 4, wherein the membrane further comprises:
   a fourth electrode between the edge support structure and the substrate, wherein the fourth electrode is electrically coupled to ground.

6. The ultrasonic transducer device of claim 1, wherein the first electrode and the second electrode each comprise a surface area to provide for capacitance matching between capacitance associated with the first electrode and capacitance associated with the second electrode.

7. The ultrasonic transducer device of claim 6, wherein positions relative to the center of the membrane of the first electrode and the second electrode are optimized to provide amplitude and phase matching over a frequency range of interest.

8. An ultrasonic transducer device comprising:
   a substrate;
   an edge support structure connected to the substrate; and
   a membrane connected to the edge support structure such that a cavity is defined between the membrane and the substrate, the membrane configured to allow movement at ultrasonic frequencies, the membrane comprising:
   a first piezoelectric layer having a first surface and a second surface;
   a second piezoelectric layer having a first surface and a second surface, wherein the second surface of the first piezoelectric layer faces the first surface of the second piezoelectric layer;
   a buffer layer between the first piezoelectric layer and the second piezoelectric layer, wherein the buffer layer has a thickness that tunes a frequency of operation of the ultrasonic transducer device to a desired frequency;
   a first electrode placed on the first surface of the first piezoelectric layer;
   a second electrode placed on the first surface of the second piezoelectric layer, such that the second electrode is disposed between the second piezoelectric layer and the buffer layer, and such that the first electrode and second electrode are on opposite sides of a neutral axis of the ultrasonic transducer device; and
   a third electrode placed on the second surface of the first piezoelectric layer, such that the third electrode is disposed between the first piezoelectric layer and the buffer layer;
   wherein, during a receive operation, the first electrode and the second electrode operate to provide differential receiving and the third electrode is electrically coupled to ground.

9. The ultrasonic transducer device of claim 8, wherein the membrane further comprises:
   a fourth electrode placed on the second surface of the second piezoelectric layer and electrically coupled to ground.

10. The ultrasonic transducer device of claim 8, wherein the first surface of the first piezoelectric layer overlies the cavity.

11. The ultrasonic transducer device of claim 8, wherein, during a transmit operation, the first electrode and the second electrode are driven with waveforms having inverse potentials.

12. The ultrasonic transducer device of claim 8, wherein, during a transmit operation, the first electrode and the second electrode are driven with waveforms having inverse potentials and the third electrode is electrically coupled to ground.

13. The ultrasonic transducer device of claim 8, wherein the first electrode is a patterned electrode comprising more than one electrode components that are electrically coupled.

14. The ultrasonic transducer device of claim 8, wherein the second electrode is a patterned electrode comprising more than one electrode components that are electrically coupled.

15. The ultrasonic transducer device of claim 8, wherein the first electrode, the second electrode and the third electrode each comprise a surface area to provide for capacitance matching between capacitance associated with the first electrode and capacitance associated with the second electrode.

16. The ultrasonic transducer device of claim 15, wherein a position relative to the center of the membrane of the first electrode is optimized to provide amplitude and phase matching over a frequency range of interest.

17. The ultrasonic transducer device of claim 15, wherein a position relative to the center of the membrane of the second electrode is optimized to provide amplitude and phase matching over a frequency range of interest.

18. An ultrasonic transducer device comprising:
   a substrate;
   a support structure connected to the substrate; and
   a membrane connected to the support structure such that a cavity is defined between the membrane and the substrate, the membrane configured to allow movement at ultrasonic frequencies, the membrane comprising:
   a first piezoelectric layer having a first surface and a second surface;
   a second piezoelectric layer having a first surface and a second surface, wherein the second surface of the first piezoelectric layer faces the first surface of the second piezoelectric layer;
   a buffer layer between the first piezoelectric layer and the second piezoelectric layer, wherein the buffer layer has a thickness that tunes a frequency of operation of the ultrasonic transducer device to a desired frequency;
   a first electrode placed on the first surface of the first piezoelectric layer, wherein the first electrode is located at a region of maximum strain of the membrane;
   a second electrode placed on the first surface of the second piezoelectric layer, wherein the second electrode is a patterned electrode comprising more than one electrode components located proximate to the support structure of the membrane, such that the second electrode is disposed between the second piezoelectric layer and the buffer layer; and
   a third electrode placed on the second surface of the first piezoelectric layer, such that the third electrode is disposed between the first piezoelectric layer and the buffer layer.

* * * * *